US012305192B2

(12) United States Patent
Kobayashi et al.

(10) Patent No.: US 12,305,192 B2
(45) Date of Patent: May 20, 2025

(54) METHOD FOR PRODUCING ARTIFICIAL RECOMBINANT RNA VIRUS STABLY RETAINING FOREIGN GENE

(71) Applicant: OSAKA UNIVERSITY, Osaka (JP)

(72) Inventors: Takeshi Kobayashi, Osaka (JP); Yuta Kanai, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 784 days.

(21) Appl. No.: 17/619,899

(22) PCT Filed: Jun. 19, 2020

(86) PCT No.: PCT/JP2020/024131
§ 371 (c)(1),
(2) Date: Dec. 16, 2021

(87) PCT Pub. No.: WO2020/256099
PCT Pub. Date: Dec. 24, 2020

(65) Prior Publication Data

US 2022/0356491 A1 Nov. 10, 2022

(30) Foreign Application Priority Data

Jun. 21, 2019 (JP) ................................ 2019-115532

(51) Int. Cl.
*C12N 15/867* (2006.01)

(52) U.S. Cl.
CPC .. *C12N 15/867* (2013.01); *C12N 2720/12321* (2013.01); *C12N 2720/12322* (2013.01); *C12N 2720/12343* (2013.01)

(58) Field of Classification Search
None
See application file for complete search history.

(56) References Cited

U.S. PATENT DOCUMENTS

| | | | |
|---|---|---|---|
| 2009/0324546 | A1 | 12/2009 | Notka et al. |
| 2011/0033429 | A1 | 2/2011 | Notka et al. |
| 2012/0270321 | A1 | 10/2012 | Dormitzer et al. |
| 2015/0104832 | A1 | 4/2015 | Notka et al. |
| 2018/0236058 | A1 | 8/2018 | Dormitzer et al. |
| 2019/0270999 | A1 | 9/2019 | Notka et al. |
| 2019/0282689 | A1 | 9/2019 | Kobayashi et al. |
| 2020/0061174 | A1 | 2/2020 | Kalla et al. |
| 2021/0155940 | A1 | 5/2021 | Notka et al. |

FOREIGN PATENT DOCUMENTS

| | | |
|---|---|---|
| CN | 102666860 | 9/2012 |
| JP | 2008-507290 | 3/2008 |
| WO | 2018/060368 | 4/2018 |
| WO | 2018/062199 | 4/2018 |

OTHER PUBLICATIONS

Willemsen A, Zwart MP. On the stability of sequences inserted into viral genomes. Virus Evol. 5(2):vez045. Published Nov. 14, 2019. doi:10.1093/ve/vez045. (Year: 2019).*
Office Action issued Aug. 26, 2023 in corresponding Chinese Patent Application No. 202080045560.2, with English-language translation.
Office Action issued Apr. 2, 2024 in corresponding Japanese Application No. 2021-526915, with English translation, 6 pages.
Extended European Search Report issued Aug. 22, 2022 in corresponding European Patent Application No. 20825608.1.
International Preliminary Report on Patentability (Chapter I) dated Dec. 30, 2021 in International (PCT) Application No. PCT/JP2020/024131.
International Search Report issued Sep. 1, 2020 in International (PCT) Application No. PCT/JP2020/024131.
Madesis, P. et al., "A hepatitis C virus core polypeptide expressed in chloroplasts detects anti-core antibodies in infected human sera", J. Biotechnol., 2010, vol. 145, p. 377-386.
Tanaka, M. et al., "Effects of codon optimization on the mRNA levels of heterologous genes in filamentous fungi", Appl. Microbiol. Biotechnol., 2014, vol. 98, p. 3859-3867.
Tokuoka, M. et al., "Codon Optimization Increases Steady-State mRNA Levels in *Aspergillus oryzae* Heterologous Gene Expression", Appl. Environ. Microbiol., 2008, vol. 74, No. 21, p. 6538-6546.
Fischer, M. D. et al., "Codon-Optimized RPGR Improves Stability and Efficacy of AAV8 Gene Therapy in Two Mouse Models of X-Linked Retinitis Pigmentosa", Mol. Ther., 2017, vol. 25, No. 8, p. 1854-1865.
Kanai, Y. et al., "Entirely plasmid-based reverse genetics system for rotaviruses" PNAS, Feb. 28, 2017, vol. 114, No. 9, pp. 2349-2354.
Kanai, Y. et al., "Development of Stable Rotavirus Reporter Expression Systems", Journal of Virology, Feb. 2019, vol. 93, Issue 4.
Gustafsson, C. et al., "Codon bias and heterologous protein Expression", Trends in Biotechnology, vol. 22, No. 7, Jul. 2004, pp. 346-353.

* cited by examiner

*Primary Examiner* — Tracy Vivlemore
*Assistant Examiner* — Fatimah Khalaf Matalkah
(74) *Attorney, Agent, or Firm* — Wenderoth, Lind & Ponack, L.L.P.

(57) ABSTRACT

Provided is a method for producing an artificial recombinant RNA virus stably expressing a foreign gene, comprising the steps of:

(1) obtaining a foreign gene having a modified codon composition similar to that of an RNA virus gene;

(2) inserting the foreign gene obtained in step (1) into an RNA virus genome; and (3) artificially synthesizing an artificial recombinant RNA virus using reverse genetics.

4 Claims, 13 Drawing Sheets

Specification includes a Sequence Listing.

Fig. 1

(A) Alanine

| Codon | RV NSP1 | NLuc | Rv-NLuc |
|---|---|---|---|
| GCA | 38 | 0 | 33 |
| GCC | 0 | 67 | 0 |
| GCG | 6 | 33 | 0 |
| GCT | 56 | 0 | 67 |

(B) Arginine

| Codon | RV NSP1 | NLuc | Rv-NLuc |
|---|---|---|---|
| AGA | 67 | 0 | 57 |
| AGG | 8 | 14 | 14 |
| CGA | 0 | 29 | 0 |
| CGC | 4 | 29 | 14 |
| CGG | 13 | 29 | 14 |
| CGT | 8 | 0 | 0 |

(C) Asparagine

| Codon | RV NSP1 | NLuc | Rv-NLuc |
|---|---|---|---|
| AAC | 20 | 75 | 38 |
| AAT | 80 | 25 | 63 |

(D) Asparate

| Codon | RV NSP1 | NLuc | Rv-NLuc |
|---|---|---|---|
| GAC | 15 | 75 | 25 |
| GAT | 85 | 25 | 75 |

(E) Cystein

| Codon | RV NSP1 | NLuc | Rv-NLuc |
|---|---|---|---|
| TGC | 29 | 100 | 0 |
| TGT | 71 | 0 | 100 |

(F) Stop

| Codon | RV NSP1 | NLuc | Rv-NLuc |
|---|---|---|---|
| TAA | 0 | 0 | 0 |
| TAG | 0 | 0 | 0 |
| TGA | 100 | 100 | 0 |

(G) Glutamine

| Codon | RV NSP1 | NLuc | Rv-NLuc |
|---|---|---|---|
| CAA | 60 | 43 | 57 |
| CAG | 40 | 57 | 43 |

(H) Glutamate

| Codon | RV NSP1 | NLuc | Rv-NLuc |
|---|---|---|---|
| GAA | 77 | 88 | 88 |
| GAG | 23 | 13 | 13 |

(I) Glycine

| Codon | RV NSP1 | NLuc | Rv-NLuc |
|---|---|---|---|
| GGA | 50 | 15 | 40 |
| GGC | 8 | 45 | 20 |
| GGG | 17 | 25 | 25 |
| GGT | 25 | 15 | 15 |

(J) Histidine

| Codon | RV NSP1 | NLuc | Rv-NLuc |
|---|---|---|---|
| CAC | 20 | 50 | 25 |
| CAT | 80 | 50 | 75 |

(K) Isoluecine

| Codon | RV NSP1 | NLuc | Rv-NLuc |
|---|---|---|---|
| ATA | 35 | 0 | 22 |
| ATC | 9 | 78 | 28 |
| ATT | 56 | 22 | 50 |

(L) Luecine

| Codon | RV NSP1 | NLuc | Rv-NLuc |
|---|---|---|---|
| CTA | 6 | 0 | 0 |
| CTC | 2 | 13 | 13 |
| CTG | 8 | 75 | 19 |
| CTT | 18 | 6 | 19 |
| TTA | 33 | 0 | 25 |
| TTG | 33 | 6 | 25 |

(M) Lysine

| Codon | RV NSP1 | NLuc | Rv-NLuc |
|---|---|---|---|
| AAA | 71 | 43 | 71 |
| AAG | 29 | 57 | 29 |

(N) Methionine

| Codon | RV NSP1 | NLuc | Rv-NLuc |
|---|---|---|---|
| ATG | 100 | 100 | 100 |

(O) Phenylalanine

| Codon | RV NSP1 | NLuc | Rv-NLuc |
|---|---|---|---|
| TTC | 16 | 63 | 25 |
| TTT | 84 | 38 | 75 |

(P) Proline

| Codon | RV NSP1 | NLuc | Rv-NLuc |
|---|---|---|---|
| CCA | 71 | 0 | 67 |
| CCC | 0 | 17 | 0 |
| CCG | 6 | 67 | 17 |
| CCT | 24 | 17 | 17 |

(Q) Serine

| Codon | RV NSP1 | NLuc | Rv-NLuc |
|---|---|---|---|
| AGC | 6 | 33 | 17 |
| AGT | 30 | 17 | 33 |
| TCA | 36 | 0 | 33 |
| TCC | 9 | 50 | 0 |
| TCG | 3 | 0 | 0 |
| TCT | 15 | 0 | 17 |

(R) Threonine

| Codon | RV NSP1 | NLuc | Rv-NLuc |
|---|---|---|---|
| ACA | 22 | 40 | 30 |
| ACC | 9 | 30 | 10 |
| ACG | 17 | 10 | 20 |
| ACT | 52 | 20 | 40 |

(S) Tryptophan

| Codon | RV NSP1 | NLuc | Rv-NLuc |
|---|---|---|---|
| TGG | 100 | 100 | 100 |

(T) Tyrosine

| Codon | RV NSP1 | NLuc | Rv-NLuc |
|---|---|---|---|
| TAC | 27 | 33 | 33 |
| TAT | 73 | 67 | 67 |

(U) Valine

| Codon | RV NSP1 | NLuc | Rv-NLuc |
|---|---|---|---|
| GTA | 18 | 22 | 22 |
| GTC | 9 | 22 | 11 |
| GTG | 23 | 44 | 28 |
| GTT | 50 | 11 | 39 |

Fig. 2

```
NLuc      1~ ATGGTCTTCACACTCGAAGATTTCGTTGGGGACTGGCGACAGACAGCCGGCTACAACCTGGACCAAGTCCTTGAACAGGGAGGTGTGTCCAGTTTGTTTC
Rv-NLuc      ........T..G...........T........T...A..........T..A......T.A..T.....T.................T..A..........

             AGAATCTGGGGGTGTCCGTAACTCCGATCGAAAGGATTGTCCTGAGCGGTGAAAATGGGCTGAAGATCGACATCCATGTCATCATCCCGTATGAAGGTCT
             ................A.......................TT.A..T..............T..A..T..............T..A..A.........T.

             GAGCGGCGACCAAATGGGCCAGATCGAAAAAATTTTTAAGGTGGTGTACCCTGTGGATGATCATCACTTTAAGGTGATCCTGCACTATGGCACACTGGTA
             ......A..T........A..A..A.................T..T....................T.....A.....A...........A..T......

             ATCGACGGGGTTACGCCGAACATGATCGACTATTTCGGACGGCCGTATGAAGGCATCGCCGTGTTCGACGGCAAAAAGATCACTGTAACAGGGACCCTGT
             ..T..T...........A..T........T.....T...A.A..A...........T..A...........A.................T.....TT...

             GGAACGGCAACAAAATTATCGACGAGCGCCTGATCAACCCCGACGGCTCCCTGCTGTTCCGAGTAACCATCAACGGAGTGACCGGCTGGCGGCTGTGCGA
             ....T.....T.......................A.....A..T.....TT.A......A.......A..T....................T..A..T..

             ACGCATTCTGGCGTGA ~516
              A.A....T..T...
```

Fig. 5

(A) Alanine

| Codon | RV NSP1 | ZsG | Rv-ZsG |
|---|---|---|---|
| GCA | 38 | 0 | 29 |
| GCC | 0 | 100 | 0 |
| GCG | 6 | 0 | 0 |
| GCT | 56 | 0 | 71 |

(B) Arginine

| Codon | RV NSP1 | ZsG | Rv-ZsG |
|---|---|---|---|
| AGA | 67 | 0 | 50 |
| AGG | 8 | 0 | 13 |
| CGA | 0 | 0 | 0 |
| CGC | 4 | 100 | 13 |
| CGG | 13 | 0 | 25 |
| CGT | 8 | 0 | 0 |

(C) Asparagine

| Codon | RV NSP1 | ZsG | Rv-ZsG |
|---|---|---|---|
| AAC | 20 | 100 | 25 |
| AAT | 80 | 0 | 75 |

(D) Asparate

| Codon | RV NSP1 | ZsG | Rv-ZsG |
|---|---|---|---|
| GAC | 15 | 100 | 13 |
| GAT | 85 | 0 | 87 |

(E) Cystein

| Codon | RV NSP1 | ZsG | Rv-ZsG |
|---|---|---|---|
| TGC | 29 | 100 | 13 |
| TGT | 71 | 0 | 88 |

(F) Stop

| Codon | RV NSP1 | ZsG | Rv-ZsG |
|---|---|---|---|
| TAA | 0 | 0 | 0 |
| TAG | 0 | 0 | 0 |
| TGA | 100 | 100 | 100 |

(G) Glutamine

| Codon | RV NSP1 | ZsG | Rv-ZsG |
|---|---|---|---|
| CAA | 60 | 0 | 57 |
| CAG | 40 | 100 | 43 |

(H) Glutamate

| Codon | RV NSP1 | ZsG | Rv-ZsG |
|---|---|---|---|
| GAA | 77 | 0 | 64 |
| GAG | 23 | 100 | 36 |

(I) Glycine

| Codon | RV NSP1 | ZsG | Rv-ZsG |
|---|---|---|---|
| GGA | 50 | 0 | 42 |
| GGC | 8 | 95 | 0 |
| GGG | 17 | 0 | 32 |
| GGT | 25 | 5 | 26 |

(J) Histidine

| Codon | RV NSP1 | ZsG | Rv-ZsG |
|---|---|---|---|
| CAC | 20 | 100 | 14 |
| CAT | 80 | 0 | 86 |

(K) Isoluecine

| Codon | RV NSP1 | ZsG | Rv-ZsG |
|---|---|---|---|
| ATA | 35 | 0 | 42 |
| ATC | 9 | 100 | 8 |
| ATT | 56 | 0 | 50 |

(L) Luecine

| Codon | RV NSP1 | ZsG | Rv-ZsG |
|---|---|---|---|
| CTA | 6 | 0 | 0 |
| CTC | 2 | 0 | 0 |
| CTG | 8 | 62 | 8 |
| CTT | 18 | 0 | 15 |
| TTA | 33 | 0 | 38 |
| TTG | 33 | 38 | 38 |

(M) Lysine

| Codon | RV NSP1 | ZsG | Rv-ZsG |
|---|---|---|---|
| AAA | 71 | 0 | 65 |
| AAG | 29 | 100 | 35 |

(N) Methionine

| Codon | RV NSP1 | ZsG | Rv-ZsG |
|---|---|---|---|
| ATG | 100 | 100 | 100 |

(O) Phenylalanine

| Codon | RV NSP1 | ZsG | Rv-ZsG |
|---|---|---|---|
| TTC | 16 | 100 | 25 |
| TTT | 84 | 0 | 75 |

(P) Proline

| Codon | RV NSP1 | ZsG | Rv-ZsG |
|---|---|---|---|
| CCA | 71 | 0 | 62 |
| CCC | 0 | 100 | 0 |
| CCG | 6 | 0 | 0 |
| CCT | 24 | 0 | 38 |

(Q) Serine

| Codon | RV NSP1 | ZsG | Rv-ZsG |
|---|---|---|---|
| AGC | 6 | 25 | 0 |
| AGT | 30 | 0 | 25 |
| TCA | 36 | 0 | 50 |
| TCC | 9 | 75 | 8 |
| TCG | 3 | 0 | 8 |
| TCT | 15 | 0 | 8 |

(R) Threonine

| Codon | RV NSP1 | ZsG | Rv-ZsG |
|---|---|---|---|
| ACA | 22 | 0 | 20 |
| ACC | 9 | 100 | 0 |
| ACG | 17 | 0 | 10 |
| ACT | 52 | 0 | 70 |

(S) Tryptophan

| Codon | RV NSP1 | ZsG | Rv-ZsG |
|---|---|---|---|
| TGG | 100 | 100 | 100 |

(T) Tyrosine

| Codon | RV NSP1 | ZsG | Rv-ZsG |
|---|---|---|---|
| TAC | 27 | 100 | 40 |
| TAT | 73 | 0 | 60 |

(U) Valine

| Codon | RV NSP1 | ZsG | Rv-ZsG |
|---|---|---|---|
| GTA | 18 | 0 | 13 |
| GTC | 9 | 7 | 0 |
| GTG | 23 | 93 | 27 |
| GTT | 50 | 0 | 60 |

Fig. 6

```
ZsG     1 ATGGCTCAGAGCAAGCACGGCCTGACCAAGGAGATGACCATGAAGTACAGAATGGAGGGCTGCGTGGACGGCCACAAGTTCGTGATCACCGGCGAGGGCA
Rv-ZsG  1 .........TCA..A..T..A..T..T..A..A.....T........T...........G..T..T..T..T..T..A..T.....T..G..G..A..A.

TCGGCTACCCCTTCAAGGGCAAGCAGGCCATCAACCTGTGCGTGGTGGAGGGCGGCCCCCTGCCCTTCGCCGAGGACATCCTGAGCGCCGCCTTCATGTACGGCAACAGA
.A..A.....A..T.....T..A..A..T..A...T.A..T.....T..A..A..T..AT....T..T..T..A..T..AT..TCA..A..T..T.....T..G..T...

GTGTTCACCGAGTACCCCCAGGACATCGTGGACTACTTCAAGAACAGCTGCCCCGCCGGCTACACCTGGGACAGAAGCTTCCTGTTCGAGGACGGCGCCGTGTGCATCTG
........T..A.....A..A..T..T..T..T..T.....A..T..T..T..T..A..G..T..A.....T...TCG..TT.A..T..A..T..T..T..T..T..T..

CAACGCCGACATCACCGTGAGCGTGGAGGAGAACTGCATGTACCACGAGAGCAAGTTCTACGGCGTGAACTTCCCCGCCGACGGCCCCGTGATGAAGAAGATGACCGACA
T..T..A..T..A..T..ATC......A........T........T...TCA..A..T.....A..T..T..T..T..T..T..A..A..T.....A........T..T.

ACTGGGAGCCCAGCTGCGAGAAGATCATCCCCGTGCCCAAGCAGGGCATCCTGAAGGGCGACGTGAGCATGTACCTGCTGCTGAAGGACGGCGGCAGACTGAGATGCCAG
.T.....A..TTCA..T..A..A..T.....A..T..T..A..A..A..AT....A..G..T..ATCA.....TT.A..TT.A.....T..G..T...T..C.G.....A

TTCGACACCGTGTACAAGGCCAAGAGCGTGCCCAGAAAGATGCCCGACTGGCACTTCATCCAGCACAAGCTGACCAGAGAGGACAGAAGCGACGCCAAGAACCAGAAGTG
........T..T..T..A..A...TGT..T..A..G..A.....A..T........T..T.....T........TC.G.....TC.C..T.....T..A..T........

GCACCTGACCGAGCACGCCATCGCCAGCGGCAGCGCCCTGCCCTGA 696
...TT.A..A.....T..T..T..T..T..ATCA..TT....A... 696
```

Fig. 9

| (A) Alanine | | | |
|---|---|---|---|
| Codon | RV NSP1 | AsR | Rv-AsR |
| GCA | 38 | 0 | 38 |
| GCC | 0 | 100 | 0 |
| GCG | 6 | 0 | 8 |
| GCT | 56 | 0 | 54 |

| (B) Arginine | | | |
|---|---|---|---|
| Codon | RV NSP1 | AsR | Rv-AsR |
| AGA | 67 | 0 | 63 |
| AGG | 8 | 13 | 13 |
| CGA | 0 | 0 | 0 |
| CGC | 4 | 88 | 13 |
| CGG | 13 | 0 | 13 |
| CGT | 8 | 0 | 0 |

| (C) Asparagine | | | |
|---|---|---|---|
| Codon | RV NSP1 | AsR | Rv-AsR |
| AAC | 20 | 100 | 33 |
| AAT | 80 | 0 | 67 |

| (D) Asparate | | | |
|---|---|---|---|
| Codon | RV NSP1 | AsR | Rv-AsR |
| GAC | 15 | 100 | 33 |
| GAT | 85 | 0 | 67 |

| (E) Cystein | | | |
|---|---|---|---|
| Codon | RV NSP1 | AsR | Rv-AsR |
| TGC | 29 | 100 | 29 |
| TGT | 71 | 0 | 71 |

| (F) Stop | | | |
|---|---|---|---|
| Codon | RV NSP1 | AsR | Rv-AsR |
| TAA | 0 | 0 | 0 |
| TAG | 0 | 0 | 0 |
| TGA | 100 | 100 | 100 |

| (G) Glutamine | | | |
|---|---|---|---|
| Codon | RV NSP1 | AsR | Rv-AsR |
| CAA | 60 | 0 | 67 |
| CAG | 40 | 100 | 33 |

| (H) Glutamate | | | |
|---|---|---|---|
| Codon | RV NSP1 | AsR | Rv-AsR |
| GAA | 77 | 0 | 84 |
| GAG | 23 | 100 | 16 |

| (I) Glycine | | | |
|---|---|---|---|
| Codon | RV NSP1 | AsR | Rv-AsR |
| GGA | 50 | 0 | 52 |
| GGC | 8 | 96 | 16 |
| GGG | 17 | 0 | 12 |
| GGT | 25 | 4 | 20 |

| (J) Histidine | | | |
|---|---|---|---|
| Codon | RV NSP1 | AsR | Rv-AsR |
| CAC | 20 | 100 | 22 |
| CAT | 80 | 0 | 78 |

| (K) Isoleucine | | | |
|---|---|---|---|
| Codon | RV NSP1 | AsR | Rv-AsR |
| ATA | 35 | 0 | 40 |
| ATC | 9 | 100 | 10 |
| ATT | 56 | 0 | 50 |

| (L) Leucine | | | |
|---|---|---|---|
| Codon | RV NSP1 | AsR | Rv-AsR |
| CTA | 6 | 0 | 6 |
| CTC | 2 | 6 | 6 |
| CTG | 8 | 89 | 6 |
| CTT | 18 | 0 | 17 |
| TTA | 33 | 0 | 33 |
| TTG | 33 | 6 | 33 |

| (M) Lysine | | | |
|---|---|---|---|
| Codon | RV NSP1 | AsR | Rv-AsR |
| AAA | 71 | 0 | 67 |
| AAG | 29 | 100 | 33 |

| (N) Methionine | | | |
|---|---|---|---|
| Codon | RV NSP1 | AsR | Rv-AsR |
| ATG | 100 | 100 | 100 |

| (O) Phenylalanine | | | |
|---|---|---|---|
| Codon | RV NSP1 | AsR | Rv-AsR |
| TTC | 16 | 100 | 27 |
| TTT | 84 | 0 | 73 |

| (P) Proline | | | |
|---|---|---|---|
| Codon | RV NSP1 | AsR | Rv-AsR |
| CCA | 71 | 0 | 62 |
| CCC | 0 | 100 | 8 |
| CCG | 6 | 0 | 8 |
| CCT | 24 | 0 | 23 |

| (Q) Serine | | | |
|---|---|---|---|
| Codon | RV NSP1 | AsR | Rv-AsR |
| AGC | 6 | 0 | 8 |
| AGT | 30 | 0 | 25 |
| TCA | 36 | 0 | 33 |
| TCC | 9 | 92 | 8 |
| TCG | 3 | 0 | 8 |
| TCT | 15 | 8 | 17 |

| (R) Threonine | | | |
|---|---|---|---|
| Codon | RV NSP1 | AsR | Rv-AsR |
| ACA | 22 | 0 | 24 |
| ACC | 9 | 100 | 6 |
| ACG | 17 | 0 | 24 |
| ACT | 52 | 0 | 47 |

| (S) Tryptophan | | | |
|---|---|---|---|
| Codon | RV NSP1 | AsR | Rv-AsR |
| TGG | 100 | 100 | 100 |

| (T) Tyrosine | | | |
|---|---|---|---|
| Codon | RV NSP1 | AsR | Rv-AsR |
| TAC | 27 | 100 | 27 |
| TAT | 73 | 0 | 73 |

| (U) Valine | | | |
|---|---|---|---|
| Codon | RV NSP1 | AsR | Rv-AsR |
| GTA | 18 | 0 | 18 |
| GTC | 9 | 0 | 0 |
| GTG | 23 | 100 | 27 |
| GTT | 50 | 0 | 55 |

Fig. 10

```
AsR     1 ATGGCCTCTTTGCTGAAGAAGACCATGCCCTTCAGGACCACCATCGAGGGCACCGTGAACGGCCACTACTTCAAGTGCACCGGCAAGGGCGAGGGCAACC
Rv-AsR  1 .....T........A.....A..A.....A..T..A..T..G.....A..A..T..A..T..A..T.....T..A..T..G.....A.....A.....T.

          CCCTGGAGGGCACCCAGGAGATGAAGATCGAGGTGATCGAGGGCGGCCCCCTGCCCTTCGCCTTCGACATCCTGTCCACCTCCTGCATGTACGGCTCCAA
          .AT.A..A.....G..A..A.........A..A..T..T..A..A..A..AT.A..T..T..A.....T..TT.A..A..TAGT........T..A....

          GGCCTTCATCAAGTACGTGTCCGGCATCCCCGACTACTTCAAGCAGTCCCTCCCCGAGGGCTTCACCTGGGAGCGCACCACCACCTACGAGGACGGCGGC
          A..T.....A..A..T..TAG..T..T..A..T..T.....A.....A.....A..A..A..T..A.....AA.G..T.....T..T........G..T

          TTCCTGACCGCCCACCAGGACACCTCCCTGGACGGCGACTGCCTGGTGTACAAGGTGAAGATCCTGGGCAACAAGTTCCCCGCCGACGGCCCCGTGATGC
          ..T..T..G..T..T..A..T..A..A..T..T..A.....TT.A..T.....A..A..A..TT....T.........T..G..A..T..G..T......

          AGAACAAGGGCGGGCGGCTGGGAGCCCTCCACCGAGATCGTGTACGAGGTGGACGGCGTGCTGCGCGGCCAGTCCCTGATGGCCCTGGAGTGCCCCGGCGG
          ....T.....T..G..G.....A...AGT..A..A..A.....T..A..T..T..A...T..A.A..A..A..G.........AT.A..A..T..A..A..

          TCGCCACCTGACCTGCCACCTGCACACCACCTACCGCTCCAAGAAGCCCGCCTCCGCCGTGAAGATGCCCGGCTTGCACTTCGAGGACCACCGCATCGAG
          ......T..T..T..T...T....T..T..T..TA.AAGT.....A..A..T..A..TT..........T..A..T..T..T..A..T...A.A..T...

          ATCCTGGAGGAGGTGGAGAAGGGCAAGTGCTACAAGCAGTACGAGGCCGCCGTGGGCCGCTACTGCGACGCCGCCCCCTCCAAGCTGGGCCACAACTGA 699
          ..AT.A..A.....T..A..A..A..A...........A..T..A..A..G..T..TA.A..T..T.....A..T..A..T..AT....A..T..T... 699
```

Fig. 11

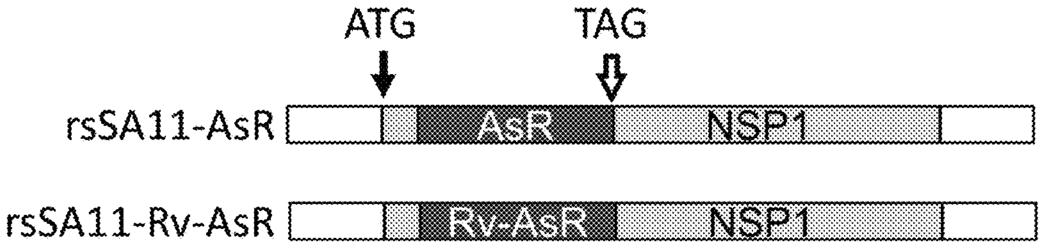

Fig. 12

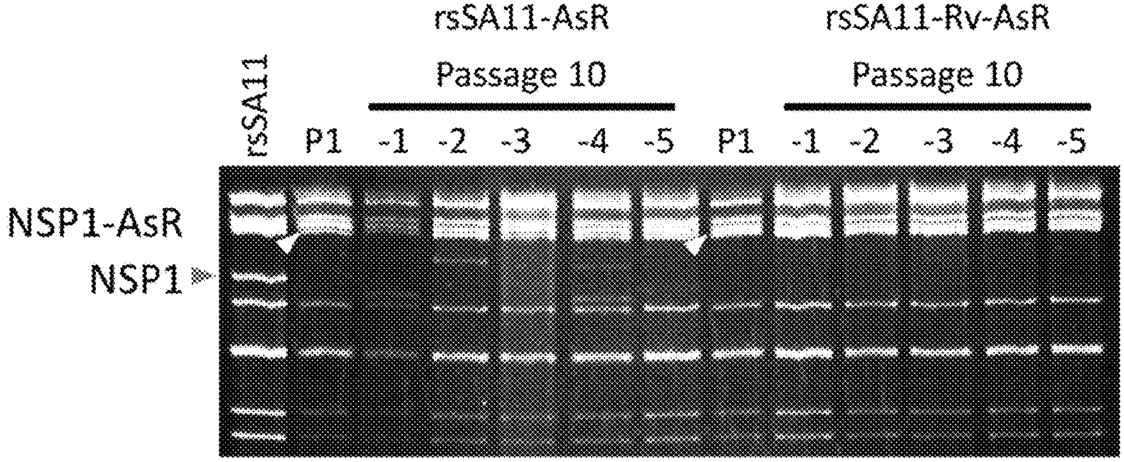

Fig. 23

(A) Alanine

| Codon | MRV L1 | ZsG | Mrv-ZsG |
|---|---|---|---|
| GCA | 29 | 0 | 29 |
| GCC | 12 | 100 | 14 |
| GCG | 29 | 0 | 29 |
| GCT | 29 | 0 | 29 |

(B) Arginine

| Codon | MRV L1 | ZsG | Mrv-ZsG |
|---|---|---|---|
| AGA | 26 | 0 | 25 |
| AGG | 12 | 0 | 12 |
| CGA | 18 | 0 | 12 |
| CGC | 10 | 100 | 12 |
| CGG | 14 | 0 | 12 |
| CGT | 21 | 0 | 25 |

(C) Asparagine

| Codon | MRV L1 | ZsG | Mrv-ZsG |
|---|---|---|---|
| AAC | 36 | 100 | 37 |
| AAT | 64 | 0 | 62 |

(D) Asparate

| Codon | MRV L1 | ZsG | Mrv-ZsG |
|---|---|---|---|
| GAC | 34 | 100 | 33 |
| GAT | 66 | 0 | 67 |

(E) Cystein

| Codon | MRV L1 | ZsG | Mrv-ZsG |
|---|---|---|---|
| TGC | 31 | 100 | 25 |
| TGT | 69 | 0 | 75 |

(F) Stop

| Codon | MRV L1 | ZsG | Mrv-ZsG |
|---|---|---|---|
| TAA | 0 | 0 | 0 |
| TAG | 0 | 0 | 0 |
| TGA | 100 | 100 | 100 |

(G) Glutamine

| Codon | MRV L1 | ZsG | Mrv-ZsG |
|---|---|---|---|
| CAA | 43 | 0 | 43 |
| CAG | 57 | 100 | 57 |

(H) Glutamate

| Codon | MRV L1 | ZsG | Mrv-ZsG |
|---|---|---|---|
| GAA | 48 | 0 | 50 |
| GAG | 52 | 100 | 50 |

(I) Glycine

| Codon | MRV L1 | ZsG | Mrv-ZsG |
|---|---|---|---|
| GGA | 33 | 0 | 32 |
| GGC | 9 | 95 | 11 |
| GGG | 20 | 0 | 21 |
| GGT | 38 | 5 | 37 |

(J) Histidine

| Codon | MRV L1 | ZsG | Mrv-ZsG |
|---|---|---|---|
| CAC | 42 | 100 | 43 |
| CAT | 58 | 0 | 57 |

(K) Isoluecine

| Codon | MRV L1 | ZsG | Mrv-ZsG |
|---|---|---|---|
| ATA | 26 | 0 | 25 |
| ATC | 23 | 100 | 25 |
| ATT | 51 | 0 | 50 |

(L) Luecine

| Codon | MRV L1 | ZsG | Mrv-ZsG |
|---|---|---|---|
| CTA | 17 | 0 | 15 |
| CTC | 3 | 0 | 0 |
| CTG | 15 | 62 | 15 |
| CTT | 11 | 0 | 8 |
| TTA | 37 | 0 | 46 |
| TTG | 17 | 38 | 15 |

(M) Lysine

| Codon | MRV L1 | ZsG | Mrv-ZsG |
|---|---|---|---|
| AAA | 44 | 0 | 45 |
| AAG | 56 | 100 | 55 |

(N) Methionine

| Codon | MRV L1 | ZsG | Mrv-ZsG |
|---|---|---|---|
| ATG | 100 | 100 | 100 |

(O) Phenylalanine

| Codon | MRV L1 | ZsG | Mrv-ZsG |
|---|---|---|---|
| TTC | 51 | 100 | 50 |
| TTT | 49 | 0 | 50 |

(P) Proline

| Codon | MRV L1 | ZsG | Mrv-ZsG |
|---|---|---|---|
| CCA | 41 | 0 | 38 |
| CCC | 13 | 100 | 15 |
| CCG | 12 | 0 | 15 |
| CCT | 33 | 0 | 31 |

(Q) Serine

| Codon | MRV L1 | ZsG | Mrv-ZsG |
|---|---|---|---|
| AGC | 12 | 25 | 8 |
| AGT | 12 | 0 | 8 |
| TCA | 27 | 0 | 33 |
| TCC | 10 | 75 | 8 |
| TCG | 12 | 0 | 8 |
| TCT | 25 | 0 | 33 |

(R) Threonine

| Codon | MRV L1 | ZsG | Mrv-ZsG |
|---|---|---|---|
| ACA | 29 | 0 | 30 |
| ACC | 6 | 100 | 0 |
| ACG | 20 | 0 | 20 |
| ACT | 46 | 0 | 50 |

(S) Tryptophan

| Codon | MRV L1 | ZsG | Mrv-ZsG |
|---|---|---|---|
| TGG | 100 | 100 | 100 |

(T) Tyrosine

| Codon | MRV L1 | ZsG | Mrv-ZsG |
|---|---|---|---|
| TAC | 39 | 100 | 40 |
| TAT | 61 | 0 | 60 |

(U) Valine

| Codon | MRV L1 | ZsG | Mrv-ZsG |
|---|---|---|---|
| GTA | 20 | 0 | 20 |
| GTC | 17 | 7 | 20 |
| GTG | 42 | 93 | 40 |
| GTT | 21 | 0 | 20 |

Fig. 24

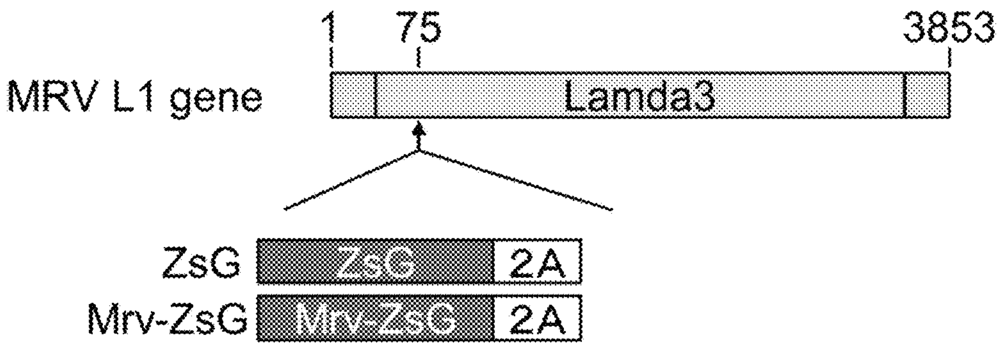

METHOD FOR PRODUCING ARTIFICIAL RECOMBINANT RNA VIRUS STABLY RETAINING FOREIGN GENE

TECHNICAL FIELD

The present invention relates to a method for producing an artificial recombinant RNA virus stably retaining a foreign gene.

BACKGROUND ART

Rotaviruses, which belong to the family Reoviridae, cause acute gastroenteritis in infants, and about 200,000 people die annually from *rotavirus* infection. There was a delay in the development of technologies to artificially produce desired rotaviruses, but the present inventors recently succeeded in developing a practical method for artificially producing rotaviruses (Patent Literature 1, Non-Patent Literature 1). This technology has made it possible to flexibly produce artificial recombinant rotaviruses having desired mutations and artificial recombinant rotaviruses carrying foreign genes. However, thereafter, the present inventors noticed that such artificial recombinant rotaviruses having foreign genes tend to lose the full-length foreign genes in a short period of time, i.e., such rotaviruses have difficulty in stably retaining and expressing the foreign genes over a long period of time. After conducting extensive research, the present inventors reported some improved methods for artificially producing rotaviruses stably retaining and expressing foreign genes (Non-Patent Literature 2).

Codon optimization is a frequently used technique to improve foreign gene expression in heterogeneous hosts by modifying the codon composition of foreign genes to be similar that of the host genes (Non-Patent Literature 3), and many codon optimization software packages are available. However, it is unknown whether codon optimization is applicable to stable retention of introduced foreign genes in artificial recombinant RNA viruses.

CITATION LIST

Patent Literature

Patent Literature 1: WO 2018/062199

Non-Patent Literature

Non-Patent Literature 1:
Kanai et al., Proc Natl Acad Sci USA, 2017 Feb. 28; 114(9):2349-2354
Non-Patent Literature 2:
Kanai et al., Journal of Virology, 2019 Feb. 5; 93(4). pii: e01774-18
Non-Patent Literature 3:
Gustafsson et al., Trends Biotechnol., 2004 July; 22(7):346-353

SUMMARY OF INVENTION

Technical Problem

An object of the present invention is to provide a method for producing an artificial recombinant RNA virus stably retaining a foreign gene and a method for enabling stable retention of an introduced foreign gene in an artificial recombinant RNA virus.

Solution to Problem

The present invention includes the following to achieve the above-mentioned object.

[1] A method for producing an artificial recombinant RNA virus stably retaining a foreign gene, comprising the steps of:

(1) obtaining a foreign gene having a modified codon composition similar to that of an RNA virus gene;

(2) inserting the foreign gene obtained in step (1) into an RNA virus genome; and (3) artificially synthesizing an artificial recombinant RNA virus using reverse genetics.

[2] The method according to the above [1], wherein the RNA virus is a virus belonging to the family Reoviridae.

[3] The method according to the above [2], wherein the virus belonging to the family Reoviridae is a virus belonging to the genus *Rotavirus* or *Orthoreovirus*.

[4] The method according to any one of the above [1] to [3], wherein the foreign gene obtained in step (1) has a codon composition modified to such an extent that the difference in the codon composition between the foreign gene and the RNA virus gene is within +30%.

[5] A method for enabling stable retention of an introduced foreign gene in an artificial recombinant RNA virus artificially synthesized using reverse genetics, comprising modifying the codon composition of a foreign gene to be similar to that of an RNA virus gene.

[6] The method according to the above [5], wherein the RNA virus is a virus belonging to the family Reoviridae.

[7] The method according to the above [6], wherein the virus belonging to the family Reoviridae is a virus belonging to the genus *Rotavirus* or *Orthoreovirus*.

[8] The method according to any one of the above [5] to [7], wherein the codon composition of the foreign gene is modified to be similar to that of the RNA virus gene to such an extent that the difference in the codon composition between the foreign gene and the RNA virus gene is within ±30%.

Advantageous Effects of Invention

This invention provides an artificial recombinant RNA virus stably retaining a foreign gene over a long period of time.

BRIEF DESCRIPTION OF DRAWINGS

FIG. 1 shows the codon compositions for each amino acid in the NSP1 gene of the simian *rotavirus* strain SA11 (RV NSP1 gene), a luciferase gene (NLuc gene), and a codon-modified luciferase gene (Rv-NLuc gene).

FIG. 2 shows the nucleotide sequences of a luciferase gene (NLuc gene) (SEQ ID NO: 12) and a codon-modified luciferase gene (Rv-NLuc gene) (SEQ ID NO: 13).

FIG. 5 shows the codon compositions for each amino acid in the NSP1 gene of the simian rotavirus strain SA11 (RV NSP1 gene), a green fluorescent protein gene (ZsG gene), and a codon-modified green fluorescent protein gene (Rv-ZsG gene).

FIG. 6 shows the nucleotide sequences of a green fluorescent protein gene (ZsG gene) (SEQ ID NO: 14) and a codon-modified green fluorescent protein gene (Rv-ZsG gene) (SEQ ID NO: 15).

FIG. 9 shows the codon compositions for each amino acid in the NSP1 gene of the simian rotavirus strain SA11 (RV NSP1 gene), a red fluorescent protein gene (AsR gene), and a codon-modified red fluorescent protein gene (Rv-AsR gene).

FIG. 10 shows the nucleotide sequences of a red fluorescent protein gene (AsR gene) (SEQ ID NO: 16) and a codon-modified red fluorescent protein gene (Rv-AsR gene) (SEQ ID NO: 17).

FIG. 11 shows the structure of a simian rotavirus SA11 NSP1 gene having an insertion of a red fluorescent protein gene (AsR gene) and the structure of a simian rotavirus SA11 NSP1 gene having an insertion of a codon-modified red fluorescent protein gene (Rv-AsR gene).

FIG. 12 shows the results of foreign gene stability evaluation after 10 passages of an artificial recombinant rotavirus having a red fluorescent protein gene (AsR gene) and an artificial recombinant rotavirus having a codon-modified red fluorescent protein gene (Rv-AsR gene).

FIG. 23 shows the codon compositions for each amino acid in the L1 gene of the mammalian reovirus T1L (MRV L1 gene), a green fluorescent protein gene (ZsG gene), and a codon-modified green fluorescent protein gene (Mrv-ZsG gene).

FIG. 24 shows the structure of a mammalian reovirus L1 gene having an insertion of a green fluorescent protein gene (ZsG gene) and the structure of a mammalian reovirus L1 gene having an insertion of a codon-modified green fluorescent protein gene (Mrv-ZsG gene).

DESCRIPTION OF EMBODIMENTS

Figure 3:
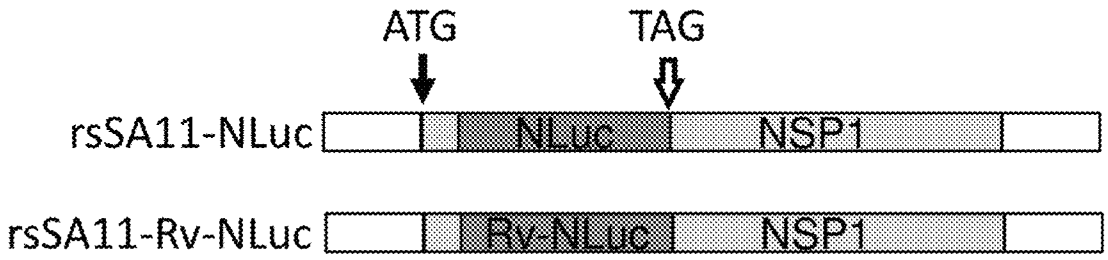
FIG. 3 shows the structure of a simian *rotavirus* SA11 NSP1 gene having an insertion of a luciferase gene (NLuc gene) and the structure of a simian *rotavirus* SA11 NSP1 gene having an insertion of a codon-modified luciferase gene (Rv-NLuc gene).

The present invention provides a method for producing an artificial recombinant RNA virus stably retaining a foreign gene (hereinafter referred to as the "production method of the present invention"). The production method at least comprises the following steps:

(1) obtaining a foreign gene having a modified codon composition similar to that of an RNA virus gene;

(2) inserting the foreign gene obtained in step (1) into an RNA virus genome; and (3) obtaining an artificial recombinant RNA virus using reverse genetics.

The RNA virus may be a double-stranded RNA virus, a positive-sense single-stranded RNA virus, or a negative-sense single-stranded RNA virus. Examples of the double-stranded RNA virus include viruses belonging to the families Reoviridae and Birnaviridae. Examples of the positive-sense single-stranded RNA virus include viruses belonging to the families Coronaviridae, Picornaviridae, Togaviridae, Flaviviridae, Caliciviridae, Astroviridae, and others. Examples of the negative-sense single-stranded RNA viruses include viruses belonging to the families Paramyxoviridae, Rhabdoviridae, Filoviridae, Orthomyxoviridae, Arenaviridae, Bunyaviridae, and others.

The RNA virus may be a virus belonging to the family Reoviridae. Viruses belonging to the family Reoviridae possess a linear double-stranded RNA (dsRNA) genome consisting of 10 to 12 segments and have an icosahedral virion of 60 to 80 nm in diameter. The viruses belonging to the family Reoviridae include viruses of the genus *Orthoreovirus* such as mammalian *orthoreovirus* (also known as mammalian reovirus), Nelson Bay *orthoreovirus* (also known as Nelson Bay reovirus or bat reovirus), and avian reovirus; viruses of the genus *Orbivirus* such as African horse sickness virus and bluetongue virus; viruses of the genus *Rotavirus* such as rotaviruses; viruses of the genus *Coltivirus* such as Colorado tick fever virus; viruses of the genus *Aquareovirus* such as *Aquareovirus* A; viruses of the genus *Cypovirus* such as cytoplasmic polyhedrosis viruses; viruses of the genus *Fijivirus* such as southern rice black-streaked dwarf virus; viruses of the genus *Phytoreovirus* such as rice dwarf virus; and viruses of the genus *Oryzavirus* such as rice ragged stunt virus. The virus belonging to the family Reoviridae may be a virus belonging to the genus *Rotavirus* or a virus belonging to the genus *Orthoreovirus*.

The foreign gene is not particularly limited. The foreign gene may be an animal gene, a plant gene, a fungal gene, a bacterial gene, or a viral gene. The base length of the foreign gene is not particularly limited and may be 10 bp or more, 100 bp or more, 500 bp or more, 1000 bp or more, 1500 bp or more, 2000 bp or more, 3000 bp or more, 4000 bp or more, or 5000 bp or more. The base length of the foreign gene may be 500 bp or less, 1000 bp or less, 1500 bp or less, 2000 bp or less, 3000 bp or less, 4000 bp or less, or 5000 bp or less.

The protein encoded by the foreign gene is not particularly limited. The protein encoded by the foreign gene may be a vaccine antigen. Examples of the vaccine antigen include norovirus antigens, adenovirus antigens, hepatitis A antigens, sapovirus antigens, hand-foot-and-mouth disease virus antigens, enterovirus antigens, HIV antigens, *Salmonella* antigens, *Campylobacter* antigens, *Vibrio parahaemolyticus* antigens, *Escherichia coli* 0157 antigens, cholera antigens, typhoid antigens, and *Shigella* antigens. These vaccine antigens may be epitope peptides.

In step (1), a foreign gene having a modified codon composition similar to that of an RNA virus gene is obtained. The codon composition of such a reference RNA virus gene may be a codon composition of a gene of the RNA virus to be used for artificial RNA virus synthesis using a codon-modified foreign gene, or a codon composition of a gene of a different RNA virus, i.e., an RNA virus that is different from the RNA virus to be used for artificial RNA virus synthesis using a codon-modified foreign gene. In the latter case, such a different RNA virus is preferably an RNA virus that is phylogenetically close to the RNA virus to be used for artificial RNA virus synthesis using a codon-modified foreign gene (e.g., a virus belonging to the same family, the same genus, different species, etc.).

The codon composition of the reference RNA virus gene may be a codon composition of all genes of the reference RNA virus, or a codon composition of some genes of the reference RNA virus. When the codon composition of some genes of an RNA virus is used as the reference, the codon composition of a single gene or two or more genes thereof may be used.

The codon composition of the reference RNA virus gene can be prepared based on the genetic information of RNA viruses registered in known gene databases (e.g., GenBank).

Table 1 shows the genome composition of all genes of the rotavirus strain SA11. Table 2 shows the genome composition of the NSP1 gene of the rotavirus strain SA11. Table 3 shows the genome composition of all genes of the bat reovirus (Pteropine *orthoreovirus*) strain MB. Table 4 shows the genome composition of all genes of the mammalian reovirus T1L. The codon compositions shown in Tables 1 to 4 can be used as the reference codon composition in the production method of the present invention. In particular, in the case where viruses belonging to the family Reoviridae, especially the genera *Rotavirus* and *Orthoreovirus*, are used for the production of artificial recombinant viruses expressing a foreign gene, these codon compositions can be used as the reference.

TABLE 1

| Genome composition (%) of all genes of the rotavirus strain SA11 | | | | | | | | |
|---|---|---|---|---|---|---|---|---|
| Alanine | GCA | 42 | Glycine | GGA | 52 | Proline | CCA | 65 |
| | GCC | 5 | | GGC | 12 | | CCC | 2 |
| | GCG | 11 | | GGG | 8 | | CCG | 12 |
| | GCT | 41 | | GGT | 28 | | CCT | 21 |
| Arginine | AGA | 64 | Histidine | CAC | 23 | Serine | AGC | 2 |
| | AGG | 15 | | CAT | 77 | | AGT | 11 |
| | CGA | 8 | Isoleucine | ATA | 47 | | TCA | 49 |
| | CGC | 4 | | ATC | 8 | | TCC | 6 |
| | CGG | 2 | | ATT | 45 | | TCG | 9 |
| | CGT | 8 | Leucine | CTA | 14 | | TCT | 23 |
| Asparagine | AAC | 24 | | CTC | 4 | Threonine | ACA | 39 |
| | AAT | 76 | | CTG | 8 | | ACC | 7 |
| Asparate | GAC | 26 | | CTT | 12 | | ACG | 15 |
| | GAT | 74 | | TTA | 38 | | ACT | 39 |
| Cystain | TGC | 31 | | TTG | 25 | Tryptophan | TGG | 100 |
| | TGT | 69 | Lysine | AAA | 74 | Tyrosine | TAG | 23 |
| Stop | TAA | 46 | | AAG | 26 | | TTA | 77 |
| | TAG | 18 | Methionine | ATG | 100 | Valine | GTA | 33 |
| | TGA | 37 | Phenylalanine | TTC | 22 | | GTC | 12 |

TABLE 1-continued

| Genome composition (%) of all genes of the rotavirus strain SA11 | | | | | | | | |
|---|---|---|---|---|---|---|---|---|
| Glutamine | CAA | 71 | | TTT | 78 | | GTG | 21 |
| | CAG | 29 | | | | | GTT | 35 |
| Glutamate | GAA | 76 | | | | | | |
| | GAH | 24 | | | | | | |

TABLE 2

| Genome composition (%) of the NSP1 gene of the rotavirus strain SA11 | | | | | | | | |
|---|---|---|---|---|---|---|---|---|
| Alanine | GCA | 38 | Glycine | GGA | 50 | Proline | CCA | 71 |
| | GCC | 0 | | GGC | 8 | | CCC | 0 |
| | GCG | 6 | | GGG | 17 | | CCG | 6 |
| | GCT | 56 | | GGT | 25 | | CCT | 24 |
| Arginine | AGA | 67 | Histidine | CAC | 20 | Serine | AGC | 6 |
| | AGG | 8 | | CAT | 80 | | AGT | 30 |
| | CGA | 0 | Isoleucine | ATA | 35 | | TCA | 30 |
| | CGC | 4 | | ATC | 9 | | TCC | 9 |
| | CGG | 13 | | ATT | 56 | | TCG | 3 |
| | CGT | 8 | Leucine | CTA | 6 | | TCT | 15 |
| Asparagine | AAC | 20 | | CTC | 2 | Threonine | ACA | 22 |
| | AAT | 80 | | CTG | 8 | | ACC | 9 |
| Asparate | GAC | 15 | | CTT | 18 | | ACG | 17 |
| | GAT | 85 | | TTA | 33 | | ACT | 52 |
| Cystain | TGC | 29 | | TTG | 33 | Tryptophan | TGG | 100 |
| | TGT | 71 | Lysine | AAA | 71 | Tyrosine | TAG | 27 |
| Stop | TAA | 0 | | AAG | 29 | | TTA | 73 |
| | TAG | 0 | Methionine | ATG | 100 | Valine | GTA | 18 |
| | TGA | 100 | Phenylalanine | TTC | 16 | | GTC | 9 |
| Glutamine | CAA | 60 | | TTT | 84 | | GTG | 23 |
| | CAG | 40 | | | | | GTT | 50 |
| Glutamate | GAA | 77 | | | | | | |
| | GAH | 23 | | | | | | |

TABLE 3

| Genome composition (%) of all genes of the bat reovirus strain MB | | | | | | | | |
|---|---|---|---|---|---|---|---|---|
| Alanine | GCA | 12 | Glycine | GGA | 16 | Proline | CCA | 28 |
| | GCC | 26 | | GGC | 19 | | CCC | 23 |
| | GCG | 12 | | GGG | 10 | | CCG | 12 |
| | GCT | 49 | | GGT | 55 | | CCT | 36 |
| Arginine | AGA | 10 | Histidine | CAC | 39 | Serine | AGC | 4 |
| | AGG | 9 | | CAT | 61 | | AGT | 13 |
| | CGA | 13 | Isoleucine | ATA | 16 | | TCA | 21 |
| | CGC | 22 | | ATC | 36 | | TCC | 23 |
| | CGG | 6 | | ATT | 49 | | TCG | 12 |
| | CGT | 40 | Leucine | CTA | 12 | | TCT | 26 |
| Asparagine | AAC | 40 | | CTC | 15 | Threonine | ACA | 17 |
| | AAT | 60 | | CTG | 22 | | ACC | 24 |
| Asparate | GAC | 39 | | CTT | 16 | | ACG | 14 |
| | GAT | 61 | | TTA | 13 | | ACT | 46 |
| Cystain | TGC | 41 | | TTG | 22 | Tryptophan | TGG | 100 |
| | TGT | 59 | Lysine | AAA | 46 | Tyrosine | TAG | 46 |
| Stop | TAA | 25 | | AAG | 54 | | TTA | 54 |
| | TAG | 42 | Methionine | ATG | 100 | Valine | GTA | 7 |
| | TGA | 33 | Phenylalanine | TTC | 56 | | GTC | 29 |
| Glutamine | CAA | 43 | | TTT | 44 | | GTG | 25 |
| | CAG | 57 | | | | | GTT | 38 |
| Glutamate | GAA | 45 | | | | | | |
| | GAH | 55 | | | | | | |

TABLE 4

| Genome composition (%) of all genes of the mammalian reovirus T1L | | | | | | | | |
|---|---|---|---|---|---|---|---|---|
| Alanine | GCA | 25 | Glycine | GGA | 32 | Proline | CCA | 39 |
| | GCC | 16 | | GGC | 18 | | CCC | 13 |
| | GCG | 23 | | GGG | 19 | | CCG | 17 |
| | GCT | 37 | | GGT | 31 | | CCT | 31 |
| Arginine | AGA | 25 | Histidine | CAC | 35 | Serine | AGC | 9 |
| | AGG | 14 | | CAT | 65 | | AGT | 13 |
| | CGA | 18 | Isoleucine | ATA | 24 | | TCA | 30 |
| | CGC | 14 | | ATC | 31 | | TCC | 12 |
| | CGG | 9 | | ATT | 45 | | TCG | 13 |
| | CGT | 21 | Leucine | CTA | 15 | | TCT | 23 |
| Asparagine | AAC | 35 | | CTC | 6 | Threonine | ACA | 25 |
| | AAT | 65 | | CTG | 20 | | ACC | 12 |
| Asparate | GAC | 36 | | CTT | 15 | | ACG | 23 |
| | GAT | 64 | | TTA | 19 | | ACT | 40 |
| Cystain | TGC | 42 | | TTG | 26 | Tryptophan | TGG | 100 |
| | TGT | 58 | Lysine | AAA | 45 | Tyrosine | TAC | 38 |
| Stop | TAA | 64 | | AAG | 55 | | TTA | 62 |
| | TAG | 0 | Methionine | ATG | 100 | Valine | GTA | 18 |
| | TGA | 36 | Phenylalanine | TTC | 49 | | GTC | 17 |
| Glutamine | CAA | 43 | | TTT | 51 | | GTG | 37 |
| | CAG | 57 | | | | | GTT | 27 |
| Glutamate | GAA | 41 | | | | | | |
| | GAH | 59 | | | | | | |

Modifying the codon composition of the foreign gene to be similar to that of the reference RNA virus gene means replacing codons in the foreign gene with codons that correspond to the same amino acids and are used more frequently in the reference RNA virus gene, without changing the amino acid composition in the foreign gene. The extent of similarity to that of the reference RNA virus gene is not particularly limited as long as the purpose of stable retention of the foreign gene can be achieved. For example, the codon composition of the foreign gene may be modified to be similar to that of the reference RNA virus gene to such an extent that the difference in the codon composition between the foreign gene and the reference RNA virus gene is within ±35%. The codon composition of the foreign gene may be modified to be similar to that of the reference RNA virus gene to such an extent that the difference in the codon composition between the foreign gene and the reference RNA virus gene is within ±30%. The codon composition of the foreign gene may be modified to be similar to that of the reference RNA virus gene to such an extent that the difference in the codon composition between the foreign gene and the reference RNA virus gene is within ±25%. The codon composition of the foreign gene may be modified to be similar to that of the reference RNA virus gene to such an extent that the difference in the codon composition between the foreign gene and the reference RNA virus gene is within ±20%. The codon composition of the foreign gene may be modified to be similar to that of the reference RNA virus gene to such an extent that the difference in the codon composition between the foreign gene and the reference RNA virus gene is within ±15%. The codon composition of the foreign gene may be modified to be similar to that of the reference RNA virus gene to such an extent that the difference in the codon composition between the foreign gene and the reference RNA virus gene is within ±10%.

The foreign gene having a modified codon composition can be obtained by DNA synthesis based on the modified nucleotide sequence. Alternatively, such a foreign gene can be obtained by introducing mutations into an original foreign gene DNA using PCR-based site-directed mutagenesis.

In step (2), the foreign gene obtained in step (1) is inserted into an RNA virus genome. The site where the foreign gene is to be inserted is not particularly limited as long as it does not interfere with artificial synthesis of the desired artificial recombinant RNA virus using reverse genetics. For example, when an artificial recombinant rotavirus is synthesized by introducing the foreign gene into a rotavirus, the foreign gene may be inserted into the NSP1 gene, the NSP3 gene, or the NSP5 gene. For example, when an artificial recombinant mammalian reovirus is synthesized by introducing the foreign gene into a mammalian reovirus, the foreign gene may be inserted into the L1 gene, the S1 gene, the S2 gene, or the S4 gene. For example, when an artificial recombinant influenza virus is synthesized by introducing the foreign gene into an influenza virus, the foreign gene may be inserted into the NS1 gene, the NA gene, or the PA gene. For example, when an artificial recombinant virus of the genus Alphavirus (Sindbis virus, Chikungunya virus, etc.) is synthesized by introducing the foreign gene into a virus of the genus Alphavirus, the foreign gene may be inserted into the NSP3 gene or the capsid gene. For example, when an artificial recombinant norovirus is synthesized by introducing the foreign gene into a norovirus, the foreign gene may be inserted into the ORF1 gene. For example, when an artificial recombinant virus of the genus Flavivirus (dengue virus, hepatitis C virus, etc.) is synthesized by introducing the foreign gene into a virus of the genus Flavivirus, the foreign gene may be inserted into the NS5A gene or the capsid gene. For example, when an artificial recombinant rhabdovirus (rabies virus, vesicular stomatitis virus, etc.) is synthesized by introducing the foreign gene into a rhabdovirus, the foreign gene may be inserted into the G protein gene. For example, when an artificial recombinant virus of the genus Picornavirus (poliovirus, foot-and-mouth disease virus, etc.) is synthesized by introducing the foreign gene into a virus of the genus Picornavirus, the foreign gene may be inserted into the P1 gene. For example, when an artificial recombinant Sendai virus is synthesized by introducing the foreign gene into a Sendai virus, the foreign gene may be inserted into the NP gene. The insertion of the foreign gene into the virus genome can be done using known genetic recombination techniques.

In step (3), an artificial recombinant RNA virus is artificially synthesized using reverse genetics. The method for artificially synthesizing an artificial recombinant RNA virus using reverse genetics can be selected from known methods as appropriate for the type of the RNA virus. Methods for synthesizing artificial recombinant rotaviruses using reverse genetics are described, for example, in Patent Literature 1, Non-Patent Literature 1, and Non-Patent Literature 2 listed above. Methods for synthesizing artificial recombinant polioviruses using reverse genetics are described, for example, in Reference 1 listed below. Methods for synthesizing artificial recombinant rabies viruses using reverse genetics are described, for example, in Reference 2 listed below. Methods for synthesizing artificial recombinant measles viruses using reverse genetics are described, for example, in Reference 3 listed below. Methods for synthesizing artificial recombinant bunyaviruses using reverse genetics are described, for example, in Reference 4 listed below. Methods for synthesizing artificial recombinant infectious bursal disease viruses using reverse genetics are described, for example, in Reference 5 listed below. Methods for synthesizing artificial recombinant hepatitis C viruses using reverse genetics is described, for example, in Reference 6 listed below. Methods for synthesizing artificial recombinant influenza viruses using reverse genetics is described, for example, in Reference 7 listed below. Methods for synthesizing artificial recombinant coronaviruses using reverse genetics is described, for example, in Reference 8 listed below. Methods for synthesizing artificial recombinant Ebola viruses using reverse genetics are described, for example, in Reference 9 listed below. Methods for synthesizing artificial recombinant bornaviruses using reverse genetics are described, for example, in Reference 10 listed below. Methods for synthesizing artificial recombinant arenaviruses using reverse genetics are described, for example, in Reference 11 listed below. Methods for synthesizing artificial recombinant reoviruses using reverse genetics are described, for example, in Reference 12 listed below. Methods for synthesizing artificial recombinant dengue viruses using reverse genetics are described, for example, in Reference 13 listed below. Methods for synthesizing artificial recombinant noroviruses using reverse genetics are described, for example, in Reference 14 listed below. Methods for synthesizing artificial recombinant Japanese encephalitis viruses using reverse genetics are described, for example, in Reference 15 listed below. Methods for synthesizing artificial recombinant bluetongue viruses using reverse genetics are described, for example, in Reference 16 listed below. Methods for synthesizing artificial recombinant human immunodeficiency viruses using reverse genetics are described, for example, in Reference 17 listed below.

REFERENCE LIST

1. Racaniello V R & Baltimore D (1981) Cloned poliovirus complementary DNA is infectious in mammalian cells. Science 214(4523):916-919.
2. Schnell M J, Mebatsion T, & Conzelmann K K (1994) Infectious Rabies Viruses from Cloned Cdna. Embo J 13(18):4195-4203.
3. Radecke F, et al. (1995) Rescue of measles viruses from cloned DNA. Embo J 14(23):5773-5784.
4. Bridgen A & Elliott R M (1996) Rescue of a segmented negative-strand RNA virus entirely from cloned complementary DNAs. Proceedings of the National Academy of Sciences of the United States of America 93(26):15400-15404.
5. Mundt E & Vakharia V N (1996) Synthetic transcripts of double-stranded Birnavirus genome are infectious. Proceedings of the National Academy of Sciences of the United States of America 93(20):11131-11136.
6. Kolykhalov A A, et al. (1997) Transmission of hepatitis C by intrahepatic inoculation with transcribed RNA. Science 277(5325):570-574.
7. Neumann G, et al. (1999) Generation of influenza A viruses entirely from cloned cDNAs. Proceedings of the National Academy of Sciences of the United States of America 96(16):9345-9350.
8. Yount B, Curtis K M, & Baric R S (2000) Strategy for systematic assembly of large RNA and DNA genomes: transmissible gastroenteritis virus model. Journal of virology 74(22):10600-10611.
9. Volchkov V E, et al. (2001) Recovery of infectious Ebola virus from complementary DNA: RNA editing of the GP gene and viral cytotoxicity. Science 291(5510):1965-1969.
10. Schneider U, Schwemmle M, & Staeheli P (2005) Genome trimming: a unique strategy for replication control employed by Borna disease virus. Proceedings of the National Academy of Sciences of the United States of America 102(9):3441-3446.
11. Sanchez A B & de la Torre J C (2006) Rescue of the prototypic Arenavirus LCMV entirely from plasmid. Virology 350(2):370-380.
12. Kobayashi T, et al. (2007) Aplasmid-based reverse genetics system for animal double-stranded RNA viruses. Cell host & microbe 1(2):147-157.
13. Lai C J, Zhao B T, Hori H, & Bray M (1991) Infectious RNA transcribed from stably cloned full-length cDNA of dengue type 4 virus. Proceedings of the National Academy of Sciences of the United States of America 88(12):5139-5143.
14. Chaudhry Y, Skinner M A, & Goodfellow I G (2007) Recovery of genetically defined murine norovirus in tissue culture by using a fowlpox virus expressing T7 RNA polymerase. The Journal of general virology 88(Pt8):2091-2100.
15. Yun S I, Kim S Y, Rice C M, & Lee Y M (2003) Development and application of a reverse genetics system for Japanese encephalitis virus. Journal of virology 77(11):6450-6465.
16. Boyce M, Celma C C, & Roy P (2008) Development of reverse genetics systems for bluetongue virus: recovery of infectious virus from synthetic RNA transcripts. Journal of virology 82(17):8339-8348.
17. Adachi A, et al. (1986) Production of acquired immunodeficiency syndrome-associated retrovirus in human and nonhuman cells transfected with an infectious molecular clone. Journal of virology 59(2):284-291.

The artificial recombinant RNA virus produced by the production method of the present invention can stably retain the foreign gene over a long period of time and stably express the foreign gene product over a long period of time. Therefore, the artificial recombinant RNA virus containing a vaccine antigen as the foreign gene would be suitable for use as a virus vaccine. In addition, the artificial recombinant RNA virus can be applied to gene therapy for genetic diseases of the gastrointestinal tract (colorectal cancer, ulcerative colitis, Crohn's disease, celiac disease, non-specific multiple ulcers of the small intestine, etc.), which are thought to be caused by genetic abnormalities, as a delivery system for a normal gene as the foreign gene to abnormal cells.

The present invention provides a method for enabling stable retention of an introduced foreign gene in an artificial recombinant RNA virus artificially synthesized using reverse genetics (hereinafter referred to as the "stable retention method of the present invention"). The stable retention method of the present invention is characterized by modifying the codon composition of a foreign gene to be similar to that of an RNA virus gene. The method for modifying the codon composition of the foreign gene to be similar to that of the reference RNA virus gene is the same as that described in the production method of the present invention above.

EXAMPLES

Hereinafter, the present invention will be described in detail by examples, but the present invention is not limited thereto.

Example 1: Artificial Recombinant Rotaviruses Expressing Luciferase 1-1 Materials and Methods (1) Virus The simian rotavirus strain SA11 was used. The present inventors previously determined and registered the nucleotide sequences of all 11 RNA genome segments of this virus strain. The names and GenBank accession numbers of the 11 individual RNA genome segments of the simian rotavirus strain SA11 (hereinafter referred to as "SA11") used in the experiment below are shown in Table 5.

TABLE 5

Sequences of genome segments of simian rotavirus strain SA11

| Genome segment | Coding protein | GenBank ACCESSION | SEQ ID NO |
|---|---|---|---|
| Segment 1 | VP1 (RNA-dependent RNA polymerase) | LC178564 | 1 |
| Segment 2 | VP2 (RNA-binding protein) | LC178565 | 2 |
| Segment 3 | VP3 (Guanylyltransferase) | LC178566 | 3 |
| Segment 4 | VP4 (Hemagglutinin, spike protein) | LC178567 | 4 |
| Segment 5 | NSP1 (Immune suppressive factor) | LC178570 | 5 |
| Segment 6 | VP6 (Inner capsid) | LC178568 | 6 |
| Segment 7 | NSP3 (Translation enhancer) | LC178572 | 7 |
| Segment 8 | NSP2 (NTPase) | LC178571 | 8 |
| Segment 9 | VP7(Outer capsid) | LC178569 | 9 |
| Segment 10 | NSP4 (Enterotoxin) | LC178573 | 10 |
| Segment 11 | NSP5 (RNA synthesis aid) | LC178574 | 11 |

(2) Plasmids Containing Expression Cassettes for Individual RNA Genome Segments (RNA Genome Segment Expression Vectors) of SA11

Plasmids containing cDNAs of the 11 individual RNA genome segments of SA11 were prepared for artificial rotavirus production. The specific procedure was as follows. The individual RNA genome segments were amplified by RT-PCR from extracted viral dsRNA as a template using the respective specific primers designed based on the nucleotide sequence of each segment. The RT-PCR products (cDNAs of the individual RNA genome segments) were individually inserted between the T7 promoter sequence and the hepatitis D virus (HDV) ribozyme sequence of plasmid p3E5 to yield plasmids each containing an expression cassette for the desired RNA genome segment (see Patent Literature 1). Each of the expression cassettes for individual RNA genome segments had a structure in which the cDNA of the corresponding segment was flanked by the T7 promoter sequence at the 5' end and the HDV ribozyme sequence at the 3' end, followed by a T7 terminator sequence. The prepared plasmids (RNA genome segment expression vectors) are designated as pT7-VP1SA11, pT7-VP2SA11, pT7-VP3SA11, pT7-VP4SA11, pT7-VP6SA11, pT7-VP7SA11, pT7-NSP1SA11, pT7-NSP2SA11, pT7-NSP3SA11, pT7-NSP4SA11, and pT7-NSP5SA11.

(3) Luciferase Gene

The NLuc gene, which is the luciferase gene of *Oplophorus gracilirostris*, was used as the luciferase gene. The NLuc protein coding region is located at positions 815 to 1330 (SEQ ID NO: 12) in the pNL1.1.TK[NLuc/TK] vector (Promega, GenBank ACCESSION: KM359774, 3817 bp).

(4) Luciferase Gene Having a Modified Codon Composition

The codon composition of the NLuc gene and the codon composition of the NSP1 gene of the rotavirus strain SA11 (hereinafter referred to as the "RV NSP1 gene") were analyzed, and based on the codon composition of both genes, the codon composition of the NLuc gene was modified to be similar to that of the RV NSP1 gene. The modified NLuc gene is designated as the "Rv-NLuc gene".

The codon compositions for each amino acid in the RV NSP1 gene, the NLuc gene, and the Rv-NLuc gene are shown in FIGS. 1A to 1U. The nucleotide sequences of the NLuc gene (SEQ ID NO: 12) and the Rv-NLuc gene (SEQ ID NO: 13) are shown in FIG. 2. In the Rv-NLuc gene, 70 of the total 516 bases of the NLuc gene were replaced. The GC content of the original NLuc gene was 53%, but the GC content of the Rv-NLuc gene was down to 40%, which was closer to the GC content of the RV NSP1 gene (31%) (see Table 6).

TABLE 6

| | GC content (%) |
|---|---|
| RV NSP1 | 31 |
| NLuc | 53 |
| Rv-NLuc | 40 |

(5) FAST Protein Expression Vector

A FAST protein expression vector was prepared by inserting the protein-coding region DNA of the Nelson Bay reovirus p10 gene (see GenBank ACCESSION: AB908284) into the BglII cleavage site of plasmid pCAGGS (5699 bp, Matsuo et al., 2006, Biochem Biophys Res Commun 340(1): 200-208) (see Patent Literature 1). The Nelson Bay reovirus p10 expression vector thus obtained is designated as pCAG-p10.

(6) Capping Enzyme Expression Vectors

Capping enzyme expression vectors were prepared by inserting the protein-coding region DNA of the vaccinia virus D1R gene (GenBank ACCESSION: NC006998, positions 93948 to 96482) or the protein-coding region DNA of the vaccinia virus D12L gene (GenBank ACCESSION: NC006998, positions 107332 to 108195) into the BglII cleavage site of the same plasmid pCAGGS as above (see Patent Literature 1). The thus obtained expression vector for the vaccinia virus mRNA capping enzyme large subunit is designated as pCAG-D1R, and the thus obtained expression vector for the vaccinia virus mRNA capping enzyme small subunit is designated as pCAG-D12L.

(7) SA11 NSP2 Protein Expression Vector

An NSP2 protein expression vector was prepared by inserting the protein-coding region DNA of the SA11 NSP2 gene (GenBank ACCESSION: LC178571, positions 47 to 1000) into the BglII cleavage site of the same plasmid pCAGGS as above (see Patent Literature 1). The SA11 NSP2 protein expression vector thus obtained is designated as pCAG-NSP2.

(8) SA11 NSP5 Protein Expression Vector

An NSP5 protein expression vector was prepared by inserting the protein-coding region DNA of the SA11 NSP5 gene (GenBank ACCESSION: LC178574, positions 22 to 618) into the BglII cleavage site of the same plasmid pCAGGS as above (see Patent Literature 1). The SA11 NSP5 protein expression vector thus obtained is designated as pCAG-NSP5.

(9) Production of Artificial Recombinant Rotaviruses Expressing Luciferase

The NLuc gene and the Rv-NLuc gene were separately amplified by PCR, and the amplified products were individually inserted between positions 128 and 129 of the NSP1 gene (SEQ ID NO: 5) of pT7-NSP1SA11 to yield an NSP1 gene expression plasmid having an NLuc gene insertion (designated as pT7-NSP1SA11-NLuc) and an NSP1 gene expression plasmid having an Rv-NLuc gene insertion (designated as pT7-NSP1SA11-Rv-NLuc) (see FIG. 3).

For the production of artificial recombinant rotaviruses expressing luciferase, 11 different plasmids were used: 10 of the 11 different plasmids containing cDNAs of the individual RNA genome segments prepared in the above (2) (excluding pT7-NSP1SA11), plus pT7-NSP1SA11-NLuc or pT7-NSP1SA11-Rv-NLuc.

On the previous day of transfection, BHK-T7/P5 cells were seeded on 6-well culture plates at $8\times10^3$ cells/well. The BHK-T7/P5 cells were transfected with 0.8 μg each of the 11 RNA genome segment expression vectors; 0.015 μg of the FAST protein expression vector (pCAG-p10); 0.8 μg each of the capping enzyme expression vectors (pCAG-D1R and pCAG-D12L), 0.8 μg of the NSP2 protein expression vector (pCAG-NSP2); and 0.8 μg of the NSP5 protein expression vector (pCAG-NSP5) using a transfection reagent (TransIT-LT1 (trade name), Mirus). The transfection reagent was used in a volume of 2 μg per microgram of DNA. The BHK-T7/P5 cells were cultured in DMEM medium supplemented with 5% FBS, 100 units/mL penicillin and 100 μg/mL streptomycin in an atmosphere of 5% $CO_2$ at 37° C. The medium and the cells were harvested 48 hours after the transfection. The harvested medium and cells were repeatedly freeze-thawed 3 times to prepare a cell lysate, and the cell lysate was added to monkey MA104 cells (ATCC CRL-2378.1) for passage. More specifically, about 0.5 mL of the cell lysate was added to confluent MA104 cells on 12-well plates in the presence of 0.5 μg/mL trypsin. The MA104 cells were cultured in FBS-free DMEM medium. In the case where the cells showed cytopathic changes during the 7 days of culture after the passage, artificial recombinant virus production was judged as a success. The virus obtained at this point is designated as P1 (Passage 1) virus. The artificial recombinant rotavirus produced using the 11 different plasmids including pT7-NSP1SA11-NLuc is designated as "rsSA11-NLuc", and the artificial recombinant rotavirus produced using the 11 different plasmids including pT7-NSP1SA11-Rv-NLuc is designated as "rsSA11-Rv-NLuc".

(10) Confirmation of Luciferase Gene Insertion by Electrophoresis

To examine the stability of the NLuc and Rv-NLuc genes after passages of rsSA11-NLuc and rsSA11-Rv-NLuc, passage of rsSA11-NLuc and rsSA11-Rv-NLuc was repeated up to P10 in MA104 cells. Confluent MA104 cells were prepared on a 12-well plate, and the medium was removed before virus infection and replaced with 1 mL of FBS-free DMEM containing 0.5 μg/ml trypsin. To the prepared MA104 cells, 1 μL of the rsSA11-NLuc P1 virus or the rsSA11-Rv-NLuc P1 virus was added, and the cells were cultured at 37° C. for 5 days. After 5 days of culture, freeze-thawing was repeated twice to yield P2 viruses. Passage was repeated in 5 wells for each recombinant virus.

Passage was repeated up to P10 to yield rsSA11-NLuc P10 virus clones 1 to 5 and rsSA11-Rv-NLuc P10 virus clones 1 to 5. Virus genomic RNA was extracted from each of the obtained P10 virus clones and subjected to SDS-PAGE together with P1 virus genomic RNAs and wild-type SA11 virus genomic RNA.

1-2 Results

Figure 4:
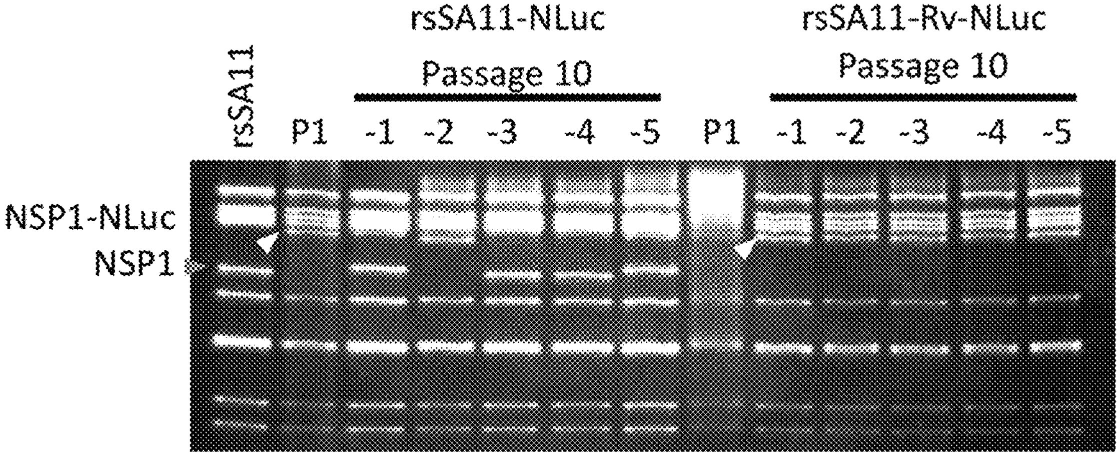
FIG. 4 shows the results of foreign gene stability evaluation after 10 passages of an artificial recombinant *rotavirus* having a luciferase gene (NLuc gene) and an artificial recombinant rotavirus having a codon-modified luciferase gene (Rv-NLuc gene).

The results are shown in FIG. 4. In the virus genomic RNA of the rsSA11-NLuc P1 virus, the NSP1-NLuc gene was found, but in the virus genomic RNAs of the rsSA11-NLuc P10 virus clones 1 to 5, the long NSP1-NLuc gene was not found. Instead, a shortened NSP1-NLuc gene was found in some clones. In contrast, in the rsSA11-Rv-NLuc P1 virus and P10 virus clones 1 to 5, only the long NSP1-Rv-NLuc gene was found. Sequencing of the shortened NSP1-NLuc gene found in the rsSA11-NLuc P10 virus showed that the NLuc gene lacked its most part. These results demonstrate that the Rv-NLuc gene is more stably retained in artificial recombinant rotaviruses than the NLuc gene.

Example 2: Artificial Recombinant Rotaviruses Expressing a Green Fluorescent Protein 2-1 Materials and Methods The ZsGreen gene (hereinafter referred to as the "ZsG gene") contained in the pZsGreen1-N1 vector (Clontech) was used as the green fluorescent protein gene. The nucleotide sequence of the ZsG gene is represented by SEQ ID NO: 14. The codon compositions of the ZsG gene and the RV NSP1 gene were analyzed, and based on the codon compositions of both genes, the codon composition of the ZsG gene was modified to be similar to that of the RV NSP1 gene. The modified ZsG gene is designated as the "Rv-ZsG gene".

The codon compositions for each amino acid in the RV NSP1 gene, the ZsG gene, and the Rv-ZsG gene are shown in FIGS. 5A to 5U. The nucleotide sequences of the ZsG gene (SEQ ID NO: 14) and the Rv-ZsG gene (SEQ ID NO: 15) are shown in FIG. 6. In the Rv-ZsG gene, 203 of the total 696 bases of the ZsG gene were replaced. The GC content of the original ZsG gene was 63%, but the GC content of the Rv-ZsG gene was down to 38%, which was closer to the GC content of the RV NSP1 gene (31%) (see Table 7).

TABLE 7

| | GC content (%) |
|---|---|
| RV NSP1 | 31 |
| ZsG | 63 |
| Rv-ZsG | 38 |

Figure 7:
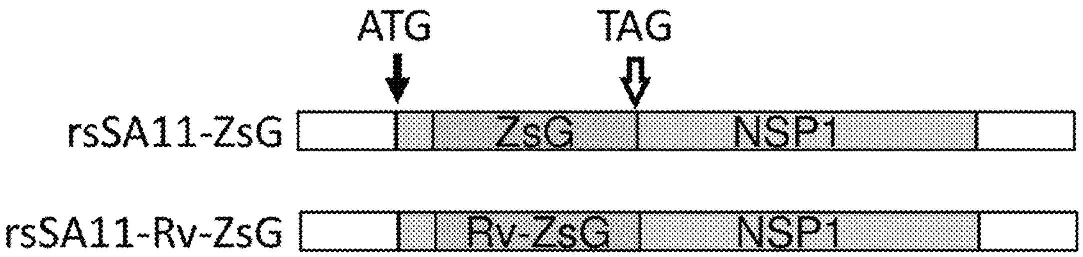
FIG. 7 shows the structure of a simian rotavirus SA11 NSP1 gene having an insertion of a green fluorescent protein gene (ZsG gene) and the structure of a simian rotavirus SA11 NSP1 gene having an insertion of a codon-modified green fluorescent protein gene (Rv-ZsG gene).

The same experiment as described in Example 1 was performed except that the ZsG gene and the Rv-ZsG gene were used instead of the NLuc gene and the Rv-NLuc gene, respectively. Specifically, the ZsG gene and the Rv-ZsG gene were separately amplified by PCR, and the amplified products were individually inserted between positions 128 and 129 of the NSP1 gene (SEQ ID NO: 5) of pT7-NSP1SA11 to yield an NSP1 gene expression plasmid having a ZsG gene insertion (designated as pT7-NSP1SA11-ZsG) and an NSP1 gene expression plasmid having an Rv-ZsG gene insertion (designated as pT7-NSP1SA11-Rv-ZsG) (see FIG. 7). In the same manner as described in Example 1 except for using these expression plasmids, artificial recombinant rotaviruses expressing a green fluorescent protein were produced. The artificial recombinant rotavirus produced using the 11 different plasmids including pT7-NSP1SA11-ZsG is designated as "rsSA11-ZsG", and the artificial recombinant rotavirus produced using the 11 different plasmids including pT7-NSP1SA11-Rv-ZsG is designated as "rsSA11-Rv-ZsG". The obtained rsSA11-ZsG and rsSA11-Rv-ZsG were separately passaged up to P10, and virus genomic RNA was extracted from each clone and subjected to SDS-PAGE.

2-2 Results

Figure 8:
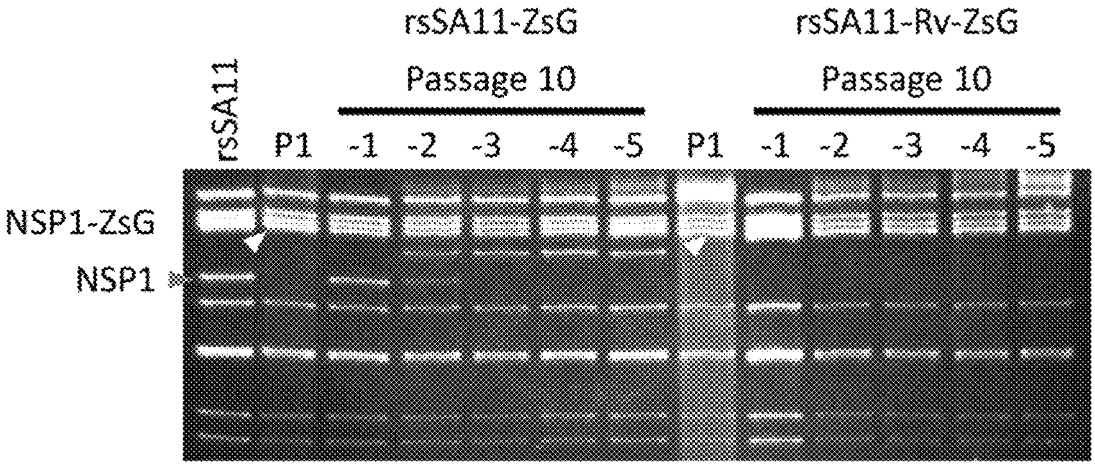
FIG. 8 shows the results of foreign gene stability evaluation after 10 passages of an artificial recombinant rotavirus having a green fluorescent protein gene (ZsG gene) and an artificial recombinant rotavirus having a codon-modified green fluorescent protein gene (Rv-ZsG gene).

The results are shown in FIG. 8. As in the results of Example 1, a shortened NSP1-ZsG gene was found in the virus genomic RNAs of the rsSA11-ZsG P10 virus clones 1 to 5. In contrast, no shortened NSP1-ZsG gene was found in rsSA11-Rv-ZsG even after 10 passages. It should be noted that the NSP1-ZsG and NSP1-Rv-ZsG genes (2306 bp) could not be identified by electrophoresis because their size is close to that of the VP4 gene (2362 bp).

Example 3: Artificial Recombinant Rotaviruses Expressing a Red Fluorescent Protein 3-1 Materials and Methods The AsRed gene (hereinafter referred to as the "AsR gene") contained in the pAsRed2-N1 vector (Clontech) was used as the red fluorescent protein gene. The nucleotide sequence of the AsR gene is represented by SEQ ID NO: 16. The codon compositions of the AsR gene and the RV NSP1 gene were analyzed, and based on the codon compositions of both genes, the codon composition of the AsR gene was modified to be similar to that of the RV NSP1 gene. The modified AsR gene is designated as the "Rv-AsR gene".

The codon compositions for each amino acid in the RV NSP1 gene, the AsR gene, and the Rv-AsR gene are shown in FIGS. 9A to 9U. The nucleotide sequences of the AsR gene (SEQ ID NO: 16) and the Rv-AsR gene (SEQ ID NO: 17) are shown in FIG. 10. In the Rv-AsR gene, 198 of the total 699 bases of the AsR gene were replaced. The GC content of the original AsR gene was 65%, but the GC content of the Rv-AsR gene was down to 40%, which is closer to the GC content of the RV NSP1 gene (31%) (see Table 8).

TABLE 8

| | GC content (%) |
|---|---|
| RV NSP1 | 31 |
| AsR | 65 |
| Rv-AsR | 40 |

The same experiment as described in Example 1 was performed except that the AsR gene and the Rv-AsR gene were used instead of the NLuc gene and the Rv-NLuc gene, respectively. Specifically, the AsR gene and the Rv-AsR gene were separately amplified by PCR, and the amplified products were individually inserted between positions 128 and 129 of the NSP1 gene (SEQ ID NO: 5) of pT7-NSP1SA11 to yield an NSP1 gene expression plasmid having an AsR gene insertion (designated as pT7-NSP1SA11-AsR) and an NSP1 gene expression plasmid having an Rv-AsR gene insertion (designated as pT7-NSP1SA11-Rv-AsR) (see FIG. 11). In the same manner as described in Example 1 except for using these expression plasmids, artificial recombinant rotaviruses expressing a red fluorescent protein were produced. The artificial recombinant rotavirus produced using the 11 different plasmids including pT7-NSP1SA11-AsR is designated as "rsSA11-AsR", and the artificial recombinant rotavirus produced using the 11 different plasmids including pT7-NSP1SA11-Rv-AsR is designated as "rsSA11-Rv-AsR". The obtained rsSA11-AsR and rsSA11-Rv-AsR were separately passaged up to P10, and virus genomic RNA was extracted from each clone and subjected to SDS-PAGE.

3-2 Results

The results are shown in FIG. 12. As in the results of Examples 1 and 2, a shortened NSP1-AsR gene was found in the virus genomic RNAs of the rsSA11-AsR P10 virus clones 1 to 5. In contrast, no shortened NSP1-AsR gene was found in rsSA11-Rv-AsR even after 10 passages. It should be noted that the NSP1-AsR and NSP1-Rv-AsR genes (2309 bp) could not be identified by electrophoresis because their size is close to that of the VP4 gene (2362 bp).

Example 4: Protein Expression Level of a Modified Foreign Gene 4-1 Materials and Methods The green fluorescent protein-expressing rsSA11-ZsG and rsSA11-Rv-ZsG produced in Example 2 and wild-type SA11 were used. Confluent MA104 cells were prepared on 12-well plates and infected with each virus at a multiplicity of infection (MOI) of 0.5 PFU/cells. The ZsG or Rv-ZsG expression at 24 hours post-infection was examined by fluorescence microscopy and quantified by western blotting. Separately, confluent MA104 cells were prepared on 12-well plates, infected with each virus at a MOI of 0.01 PFU/cells, and cultured in FBS-free DMEM containing 0.5 μg/ml trypsin. The cells were freeze-thawed twice at 24 hours post-infection, and the viral titer in the cell lysate was measured.

4-2 Results

Figure 13:
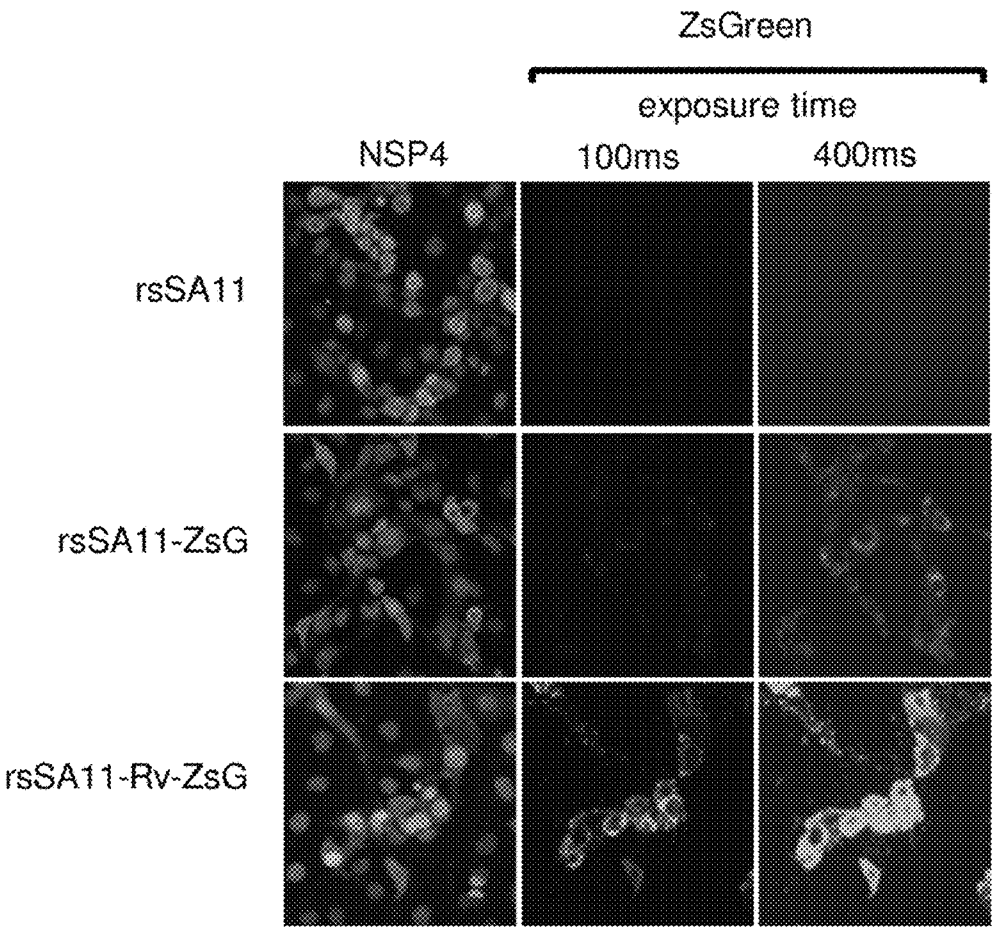
FIG. 13 shows the results of fluorescence microscopy for observing green fluorescent protein expression in an artificial recombinant rotavirus having a green fluorescent protein gene (ZsG gene) and an artificial recombinant rotavirus having a codon-modified green fluorescent protein gene (Rv-ZsG gene).
Figure 14:
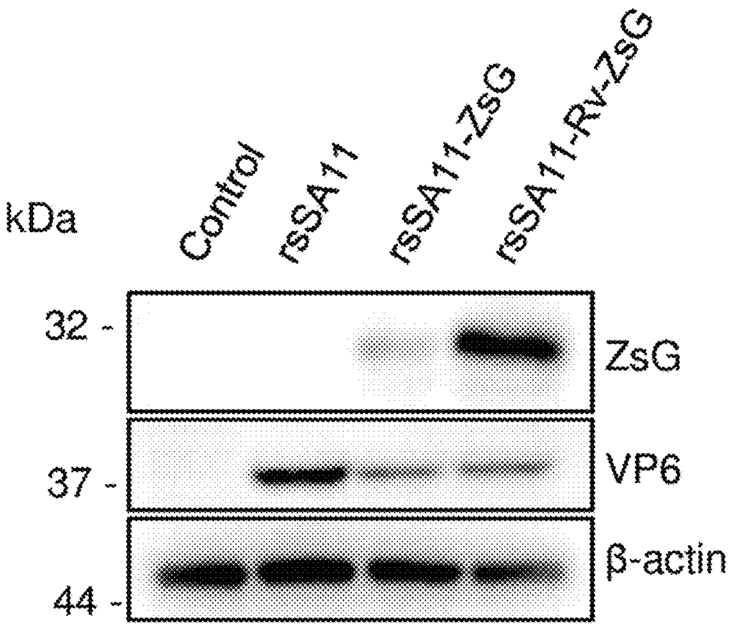
FIG. 14 shows the results of western blotting for quantifying green fluorescent protein expression in an artificial recombinant rotavirus having a green fluorescent protein gene (ZsG gene) and an artificial recombinant rotavirus having a codon-modified green fluorescent protein gene (Rv-ZsG gene).
Figure 15:
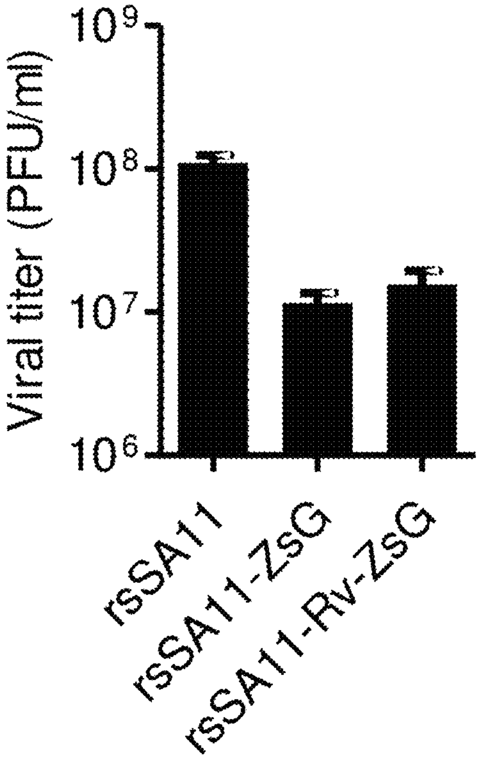
FIG. 15 shows the results of the comparison of the proliferation capabilities of an artificial recombinant rotavirus having a green fluorescent protein gene (ZsG gene) and an artificial recombinant rotavirus having a codon-modified green fluorescent protein gene (Rv-ZsG gene).

The fluorescence microscopic images are shown in FIG. 13, the results of western blotting are shown in FIG. 14, and the results of viral titer measurement are shown in FIG. 15. The green fluorescence from ZsG or Rv-ZsG was examined under a fluorescence microscope (Nikon) with an exposure time of 100 msec or 400 msec. The green fluorescence from Rv-ZsG was stronger than that from ZsG (FIG. 13). In addition, western blotting using a ZsG protein-specific antibody also showed stronger expression of Rv-ZsG (FIG. 14). On the other hand, the proliferation capacities of rsSA11-ZsG and rsSA11-Rv-ZsG were comparable (FIG. 15), indicating that the difference between ZsG and Rv-ZsG expression levels was not related to viral proliferation capacity.

Reference Example 1: Protein Expression Level of a Modified Foreign Gene

The red fluorescent protein-expressing rsSA11-AsR and rsSA11-Rv-AsR produced in Example 3 were used. As in Example 4, confluent MA104 cells were prepared on 12-well plates and infected with each virus at a multiplicity of infection (MOI) of 0.5 PFU/cell, and the AsR or Rv-AsR expression at 24 hours post-infection was examined by fluorescence microscopy.

Figure 16:
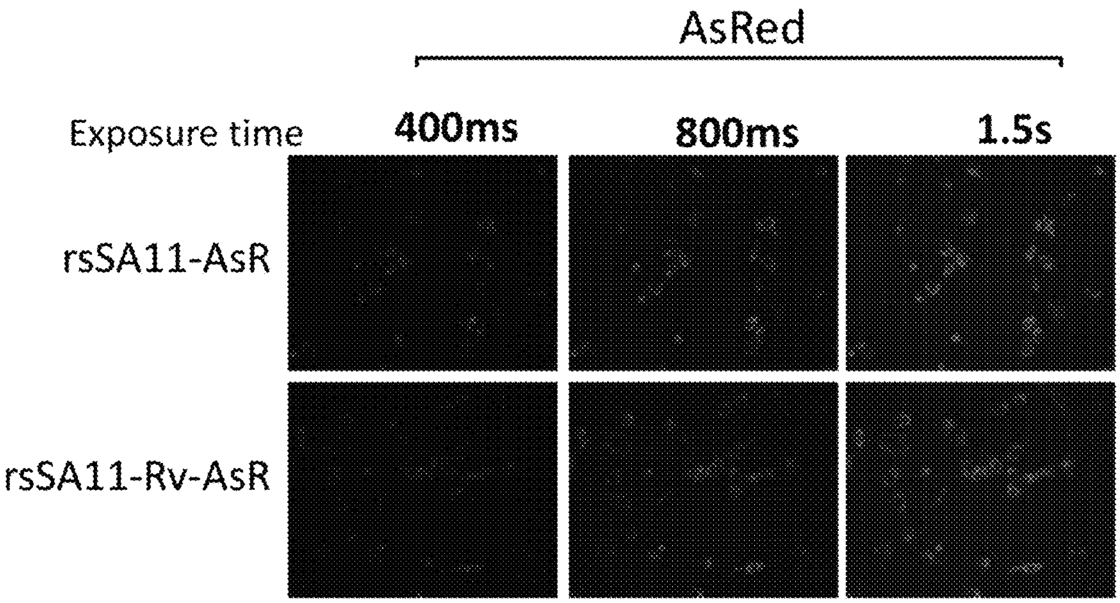
FIG. 16 shows the results of fluorescence microscopy for observing red fluorescent protein expression in an artificial recombinant rotavirus having a red fluorescent protein gene (AsR gene) and an artificial recombinant rotavirus having a codon-modified red fluorescent protein gene (Rv-AsR gene).

The results are shown in FIG. 16. The red fluorescence from AsR or Rv-AsR was examined under a fluorescence microscope (Nikon) with an exposure time of 400 ms, 800 ms, or 1.5 s. There was no difference in red fluorescence between AsR and Rv-AsR. This indicates that there was no difference between AsR and Rv-AsR expression levels.

Reference Example 2: Protein Expression Level of a Modified Foreign Gene

The luciferase-expressing rsSA11-NLuc and rsSA11-Rv-NLuc produced in Example 1 and wild-type SA11 were used. Confluent MA104 cells were prepared on 12-well plates and infected with each virus at a multiplicity of infection (MOI) of 0.1 PFU/cell, and the NLuc or Rv-NLuc expression was quantified in terms of luciferase activity (luminescence intensity) at 24 hours post-infection.

Figure 17:
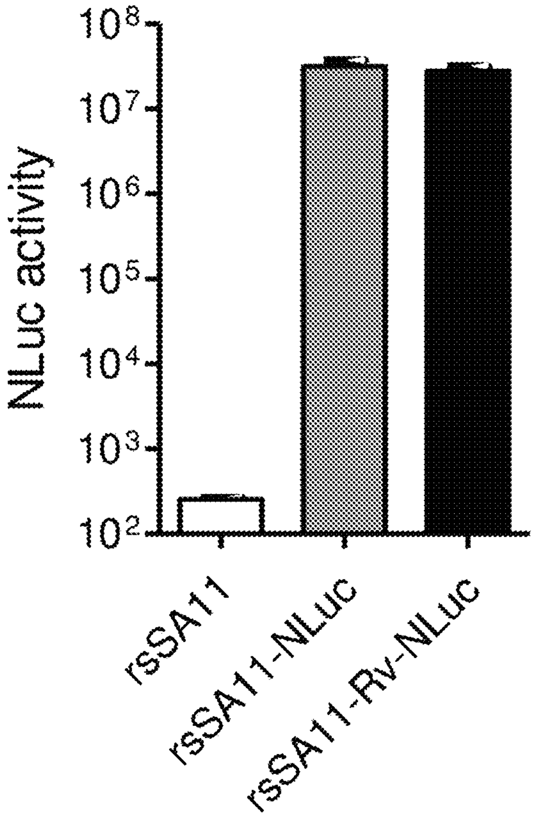
FIG. 17 shows the luciferase activity measured for an artificial recombinant rotavirus having a luciferase gene (NLuc gene) and an artificial recombinant rotavirus having a codon-modified luciferase gene (Rv-NLuc gene).

The results are shown in FIG. 17. There was no difference in luciferase activity between rsSA11-NLuc and rsSA11-Rv-NLuc. This indicates that there was no difference between NLuc and Rv-NLuc expression levels.

Example 5: Artificial Recombinant *Rotavirus* Expressing a 1.6-kbp Foreign Gene

An experiment was performed to examine whether an artificial recombinant rotavirus expressing a foreign gene with a long base length of 1 kbp or more could be produced.

5-1 Materials and Methods (1) Foreign Genes

The following foreign genes were used: a modified Akaluc gene (hereinafter referred to as the "Rv-Akaluc gene"), which was obtained by modifying the codon composition of the Akaluc gene (GenBank ACCESSION: LC320664, 1653 bp), which is a modified form of the firefly luciferase (FLuc) gene, to be similar to the codon composition of the RV NSP1 gene; and a modified norovirus VP1 gene (hereinafter referred to as the "Rv-NoV VP1 gene"), which was obtained by modifying the codon composition of the norovirus VP1 gene (GenBank ACCESSION: KM268107, 1623 bp) to be similar to the codon composition of the RV NSP1 gene. The nucleotide sequence of the modified Akaluc gene is represented by SEQ ID NO: 18, and the nucleotide sequence of the modified norovirus VP1 gene is represented by SEQ ID NO: 19.

(2) Preparation of NSP1 Expression Plasmids Having a Foreign Gene Insertion

Figure 18:
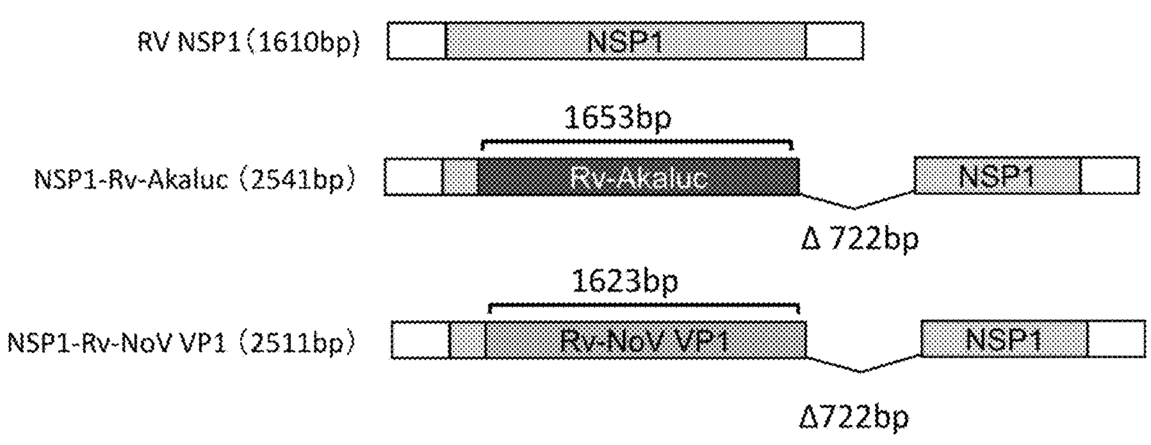
FIG. 18 shows the structure of the wild-type NSP1 gene of the simian rotavirus strain SA11, the structure of a simian rotavirus SA11 NSP1 gene having an insertion of a codon-modified firefly luciferase gene (Rv-Akaluc gene), and the structure of a simian rotavirus SA11 NSP1 gene having an insertion of a codon-modified norovirus VP1 gene (Rv-NoV VP1 gene).

The Rv-Akaluc gene and the Rv-NoV VP1 gene were separately amplified by PCR, and the amplified products were individually inserted between positions 128 and 129 of the NSP1 gene (SEQ ID NO: 5) of pT7-NSP1SA11. In addition, as described in Kanai et al. (Non-Patent Literature 2), a 722-bp region in the NSP1 gene was deleted to yield an NSP1 gene expression plasmid having an Rv-Akaluc gene insertion (designated as pT7-NSP1SA11-Rv-Akaluc) and an NSP1 gene expression plasmid having an Rv-NoV VP1 gene insertion (designated as pT7-NSP1SA11-Rv-NoV VP1) (see FIG. 18).

(3) Production of Artificial Recombinant Viruses and Confirmation of Foreign Gene Retention An artificial recombinant rotavirus expressing Rv-Akaluc and an artificial recombinant rotavirus expressing Rv-NoV VP1 were produced in the same manner as described in Example 1. The artificial recombinant rotavirus produced using the 11 different plasmids including pT7-NSP1SA11-Rv-Akaluc is designated as "rsSA11-Rv-Akaluc", and the artificial recombinant rotavirus produced using the 11 different plasmids including pT7-NSP1SA11-Rv-NoV VP1 is designated as "rsSA11-Rv-NoV VP1". The obtained rsSA11-Rv-Akaluc and rsSA11-Rv-NoV VP1 were separately passaged up to P10, and virus genomic RNA was extracted from each clone and subjected to SDS-PAGE.

5-2 Results

Figure 19:
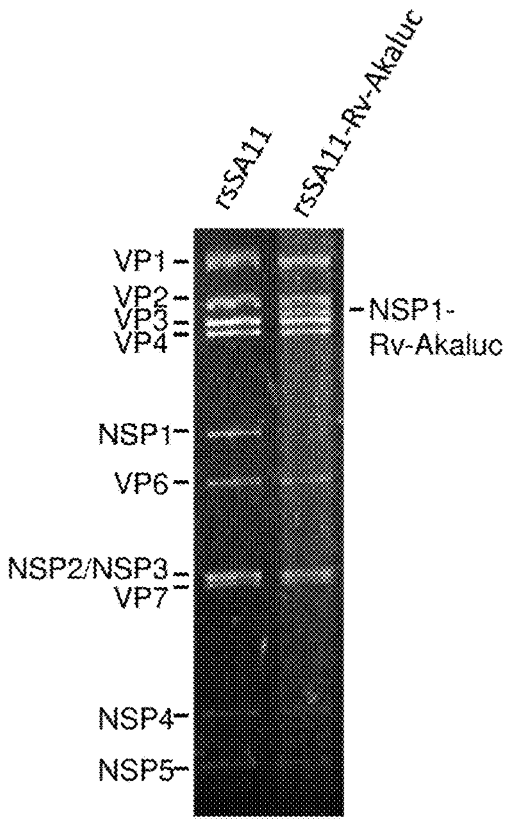
FIG. 19 shows the results of foreign gene stability evaluation after 10 passages of an artificial recombinant rotavirus having a codon-modified firefly luciferase gene (Rv-Akaluc gene).
Figure 20:
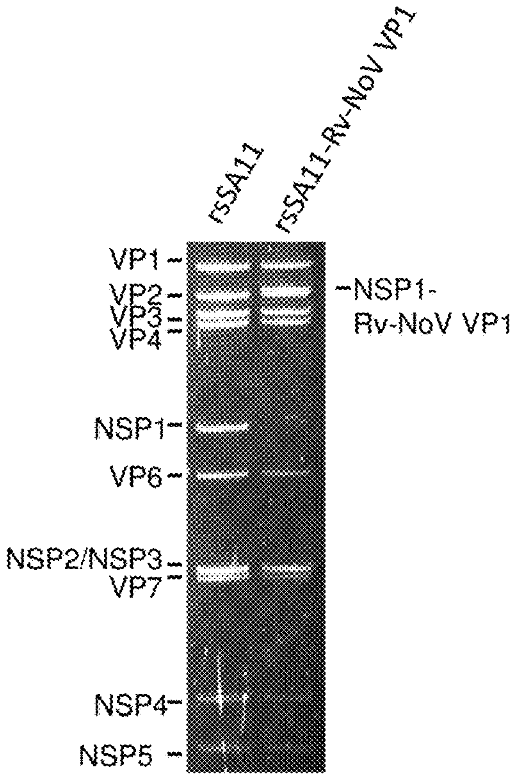
FIG. 20 shows the results of foreign gene stability evaluation after 10 passages of an artificial recombinant rotavirus having a codon-modified norovirus VP1 gene (Rv-NoV VP1 gene).

The results for rsSA11-Rv-Akaluc are shown in FIG. 19, and the results for rsSA11-Rv-NoV VP1 are shown in FIG. 20. All bands for the RNA genome segments of rsSA11-Rv-Akaluc or rsSA11-Rv-NoV VP1 were found at the same positions as those of the wild-type SA11, except for NSP1. On the other hand, the band for the NSP1-Rv-Akaluc gene of rsSA11-Rv-Akaluc and the band for the Rv-NoV VP1 gene of rsSA11-Rv-NoV VP1 were found at a higher position than the band for NSP1 of the wild-type SA11. These results indicate that recombinant rotaviruses stably retaining a foreign gene with a long base length of 1 kbp or more can be produced by modifying the codon composition of the foreign gene to be similar to that of rotaviruses.

Example 6: Artificial Recombinant Bat Reoviruses Expressing a Green Fluorescent Protein 6-1 Materials and Methods (1) Virus Bat reovirus (Pteropine *orthoreovirus*, hereinafter referred to as "PRV") belongs to the same family (Reoviridae) as rotaviruses and has a 10-segmented dsRNA consisting of L1, L2, L3, M1, M2, M3, S1, S2, S3, and S4. Plasmids containing cDNAs of the 10 individual RNA genome segments of PRV were prepared in the same manner as described in Example 1 for the preparation of plasmids containing expression cassettes for individual RNA genome segments of the rotavirus ("RNA genome segment expression vectors").

(2) Green Fluorescent Protein Genes

Figure 21:
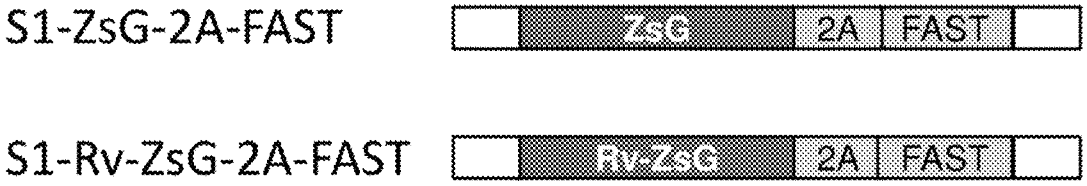
FIG. 21 shows the structure of a bat reovirus S1 gene having an insertion of a green fluorescent protein gene (ZsG gene) and the structure of a bat reovirus S1 gene having an insertion of a codon-modified green fluorescent protein gene (Rv-ZsG gene).

The same ZsG and Rv-ZsG genes as in Example 2 were used. The ZsG and Rv-ZsG genes were separately inserted into the PRV S1 gene. The PRV S1 gene encodes FAST, p17, and sigmaC. The sequence of FAST-p17-sigmaC in the PRV S1 gene was replaced with ZsG-2A-FAST or RvZsG-2A-FAST to yield the S1-ZsG-2A-FAST gene and the S1-RvZsG-2A-FAST gene (see FIG. 21).

(3) Production of Artificial Recombinant Bat Reoviruses Expressing a Green Fluorescent Protein Nine plasmids containing wild-type genes other than the S1 gene and the plasmid containing the S1-ZsG-2A-FAST gene were transfected into BHK-T7/P5 cells in the same manner as described in Example 1, and the obtained virus was passaged in monkey MA104 cells to produce an artificial recombinant bat reovirus ("rsMB-ZsG-2A-FAST"). Similarly, 9 plasmids containing wild-type genes other than the S1 gene and the plasmid containing the S1-Rv-ZsG-2A-FAST gene were transfected into BHK-T7/P5 cells, and the obtained virus was passaged in monkey MA104 cells to produce an artificial recombinant bat reovirus ("rsMB-Rv-ZsG-2A-FAST").

6-2 Results

Figure 22:
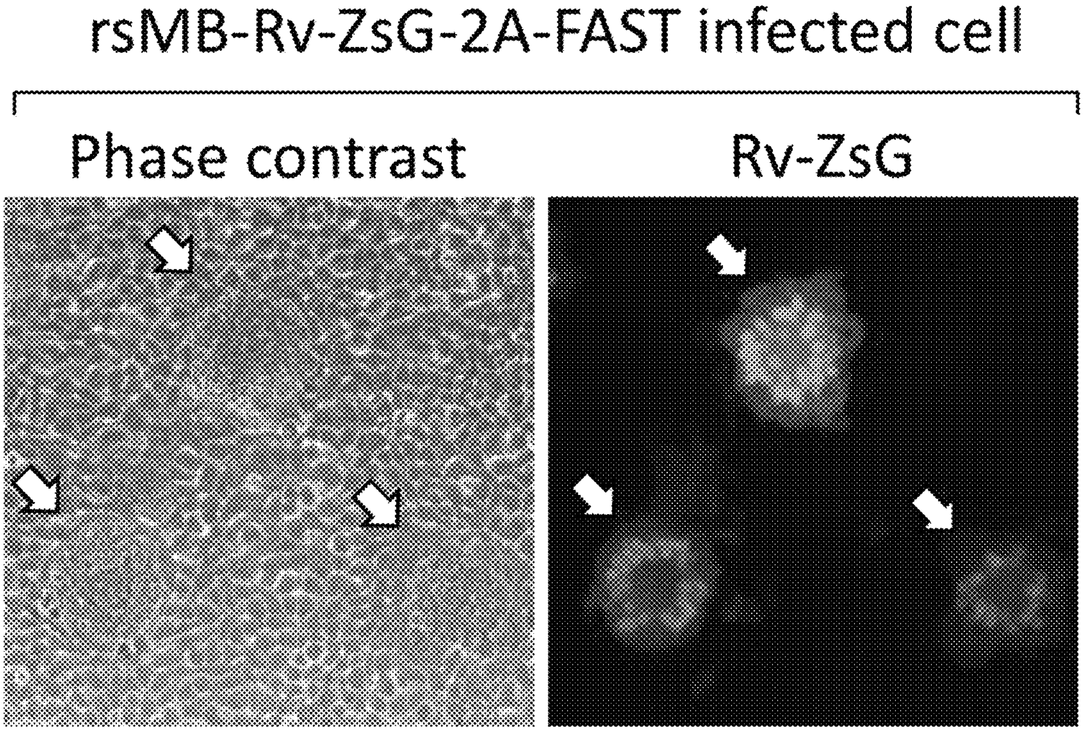
FIG. 22 shows phase-contrast (left) and fluorescence (right) microscopic images of cells infected with an artificial recombinant bat reovirus having a codon-modified green fluorescent protein gene (Rv-ZsG gene).

The green fluorescent protein (ZsG) expression in the rsMB-ZsG-2A-FAST virus was examined by the plaque assay using fluorescence microscopy. The results showed that about 1/50 to 1/100 of all virus particles emitted green fluorescence. However, after 2 or 3 viral passages, no virus emitted green fluorescence. On the other hand, 100% of the rsMB-Rv-ZsG-2A-FAST viruses emitted green fluorescence, and even after 2 or 3 viral passages, the viruses emitted green fluorescence (see FIG. 22), indicating that the Rv-ZsG gene was stably retained.

Example 7: Artificial Recombinant Mammalian Reoviruses Expressing a Green Fluorescent Protein 7-1 Materials and Methods (1) Virus Mammalian reovirus (MRV) belongs to the same family (Reoviridae) as rotaviruses and has a 10-segmented dsRNA consisting of L1, L2, L3, M1, M2, M3, S1, S2, S3, and S4. Plasmids containing cDNAs of the 10 individual RNA genome segments of MRV were prepared in the same manner as described in Example 1 for the preparation of plasmids containing expression cassettes for individual RNA genome segments of the rotavirus ("RNA genome segment expression vectors").

(2) Green Fluorescent Protein Genes

The ZsG gene and the Mrv-ZsG gene, which was obtained by modifying the codon composition of the ZsG gene to be similar to that of the MRV L1 gene, were used as green fluorescent protein genes. The codon compositions for each amino acid in the MRV L1 gene, the ZsG gene, and the Mrv-ZsG gene are shown in FIGS. 23A to 23U. The GC content of the original ZsG gene was 63%, but the GC content of the Mrv-ZsG gene was down to 43%, which was closer to the GC content of the MRV L1 gene (46%) (see Table 9).

TABLE 9

| | GC content (%) |
|---|---|
| MRV L1 | 46 |
| ZsG | 63 |
| Mrv-ZsG | 43 |

The ZsG gene and the Mrv-ZsG gene were separately inserted into the MRV L1 gene. The MRV L1 gene encodes the lamda3 protein. The 2A gene, which encodes a self-cleaving peptide, was inserted downstream of the ZsG gene or the Mrv-ZsG gene to yield L1-ZsG-2A-Lamda3 and L1-Mrv-ZsG-2A-Lamda3 (see FIG. 24).

(3) Production of Artificial Recombinant Mammalian Reoviruses Expressing a Green Fluorescent Protein Nine plasmids containing wild-type genes other than the L1 gene and the plasmid containing the L1-ZsG-2A-Lamda3 gene were transfected into BHK-T7/P5 cells in the same manner as described in Example 1, and the obtained virus was passaged in mouse L929 cells to produce an artificial recombinant mammalian reovirus ("rsMRV-ZsG"). Similarly, 9 plasmids containing wild-type genes other than the L1 gene and the plasmid containing the L1-Mrv-ZsG-2A-Lamda3 gene were transfected into BHK-T7/P5 cells, and the obtained virus was passaged in mouse L929 cells to produce an artificial recombinant mammalian reovirus ("rsMRV-Mrv-ZsG").

7-2 Results

Figure 25:
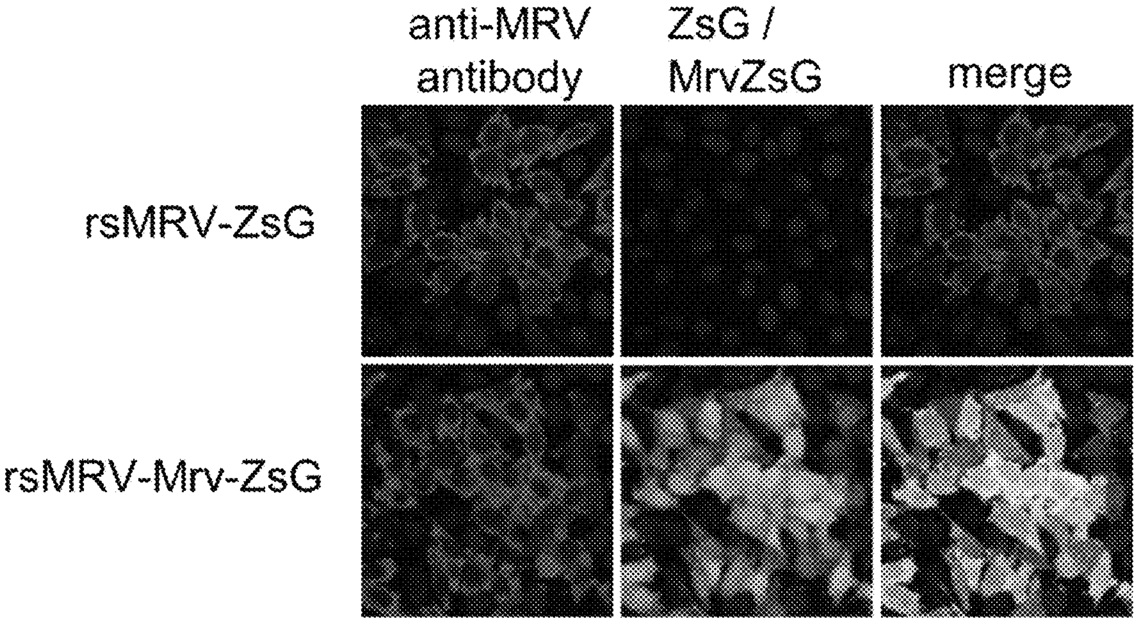
FIG. 25 shows the results of fluorescence microscopy for observing green fluorescent protein (ZsG) expression in cells subjected to infection with an artificial recombinant mammalian reovirus having a green fluorescent protein gene (ZsG gene) or a codon-modified green fluorescent protein gene (Mrv-ZsG gene) and subsequent immunostaining with an MRV-specific antibody. The top panels show cells infected with the mammalian reovirus having a ZsG gene, and the bottom panels show cells infected with the mammalian reovirus having an Mrv-ZsG gene. The left panels show the images of cells immunostained with an MRV-specific antibody, the center panels show the images of green fluorescent protein-expressing cells, and the right panels show the merged images of the left and center images.
Figure 26:
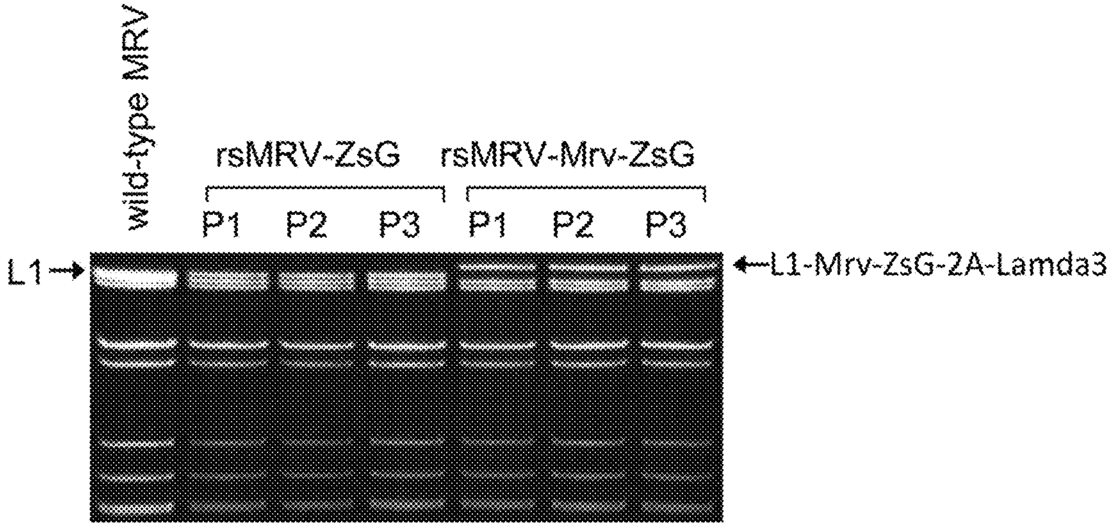
FIG. 26 shows the results of foreign gene stability evaluation after 1 to 3 passages of an artificial recombinant mammalian reovirus having a green fluorescent protein gene (ZsG gene) and an artificial recombinant mammalian reovirus having a codon-modified green fluorescent protein gene (Mrv-ZsG gene).

The green fluorescent protein (ZsG) expression in the rsMRV-ZsG virus was examined by immunostaining with an MRV-specific antibody using fluorescence microscopy. The results showed that none of the examined rsMRV-ZsG virus-infected cells emitted green fluorescence. On the other hand, 100% of the rsMRV-Mrv-ZsG virus-infected cells emitted green fluorescence, and even after 3 viral passages, the viruses emitted green fluorescence (see FIG. 25), indicating that the Mrv-ZsG gene was stably retained. Separately, virus genomic RNAs were extracted from rsMRV-ZsG and rsMRV-Mrv-ZsG after 1 to 3 passages and subjected to electrophoresis. The rsMRV-ZsG virus lacked the inserted ZsG gene at the time of the first passage, whereas the rsMRV-Mrv-ZsG virus retained the Mrv-ZsG gene even after 3 passages (see FIG. 26).

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for producing an artificial recombinant RNA virus stably retaining a foreign gene, comprising the steps of:

(1) obtaining a foreign gene having a codon composition modified to such an extent that the difference in the codon composition between the foreign gene and an RNA virus gene is within +30%;

(2) inserting the foreign gene obtained in step (1) into an RNA virus genome; and (3) artificially synthesizing an artificial recombinant RNA virus using reverse genetics, wherein the RNA virus is a virus belonging to the family Reoviridae.

2. The method according to claim 1, wherein the virus belonging to the family Reoviridae is a virus belonging to the genus Rotavirus or Orthoreovirus.

3. A method for enabling stable retention of an introduced foreign gene in an artificial recombinant RNA virus artificially synthesized using reverse genetics, comprising modifying the codon composition of a foreign gene to such an extent that the difference in the codon composition between the foreign gene and an RNA virus gene is within +30%, wherein the RNA virus is a virus belonging to the family Reoviridae.

4. The method according to claim 3, wherein the virus belonging to the family Reoviridae is a virus belonging to the genus Rotavirus or Orthoreovirus.

* * * * *

SEQUENCE LISTING

```
<160> NUMBER OF SEQ ID NOS: 19

<210> SEQ ID NO 1
<211> LENGTH: 3302
<212> TYPE: DNA
<213> ORGANISM: Rotavirus strain SA11

<400> SEQUENCE: 1

ggctattaaa gctgtacaat ggggaagtac aatctaatct tgtcagaata tctatcattt      60

atatataatt cacaatctgc agttcaaatt ccaatatatt actcttccaa cagtgaatta     120
```

-continued

```
gaaaatagat gtattgaatt tcattccaag tgtttagaga actcaaagaa tgggttatcg    180
ttaagaaagt tgtttgttga atataatgat gtcatagaaa atgccacatt actgtcaata    240
ctatcatatt cttacgacaa gtataacgct gttgaaagaa aattggtgaa gtatgcgaaa    300
ggcaaaccat tggaggcaga cttaacagtg aatgaattgg attatgagaa caataaaata    360
acatctgaat tatttccaac agcggaggaa tatacggact cactaatgga tccagcaatt    420
ttaacttcgc tatcatcaaa tttaaatgca gtcatgttct ggttggaaaa acatgaaaat    480
gatgtcgctg aaaaacttaa agtttataaa aggagattag acctattcac catagtagcc    540
tcaacgataa ataaatatgg cgtaccaagg cataacgcaa agtacagata tgaatacgac    600
gtaatgaaag ataaaccgta ctacttagtg acatgggcaa attcttcaat tgaaatgtta    660
atgtcagttt tctctcatga cgactatttg atagcaaaag agttaatagt gttatcatat    720
tctaatagat ctactctagc aaagttagtg tcatcaccaa tgtcgatttt ggtagccttg    780
gtggatatta atggaacatt tattacaaat gaagaattag aattggaatt ttcaaataaa    840
tatgtacgag caatagttcc ggatcaaaca tttgacgaat taaatcaaat gcttgacaat    900
atgaggaaag ctggattagt tgacatacct aagatgatac aggactggtt agttgatcgt    960
tctatcgaaa aatttccatt aatggctaag atatattcat ggtcgtttca tgttggattt   1020
agaaagcaaa aatgctaga tgctgcgctg gatcaattga aaactgagta tacagaaaat    1080
gtggacgatg aaatgtatcg ggaatataca atgttaataa gagatgaagt agttaaaatg   1140
cttgaagaac cagttaaaca tgatgatcac ttgctacgag attctgagtt agctggttta   1200
ctatcaatgt cgtcagcatc gaatggtgag tcaaggcagc taaagtttgg taggaaaaca   1260
attttttcaa ctaaaaagaa tatgcatgtc atggatgata tggctaacga aagatacacg   1320
cctggtataa taccaccagt gaatgttgat aaaccaatac cattaggaag aagagatgtt   1380
ccaggaagaa ggactagaat aatattcatt ctgccatacg aatatttcat agcacagcac   1440
gctgtagttg aaaaaatgtt gatttacgca aaacatacga gagaatacgc tgaattttat   1500
tcacaatcaa accaattatt gtcatacggc gatgtaacgc gtttttgtc taataacaca   1560
atggtcttgt atacggatgt atctcagtgg gattcgtctc agcataatac acagccattt   1620
aggaaaggaa taataatggg actggacata ttagctaaca tgactaatga tgctaaagtt   1680
cttcagacat taaacttata caaacaaaca caaatcaatc tcatggattc atacgttcaa   1740
ataccagatg gcaacgtcat taagaaaata caatacgggg cagtagcatc aggagagaaa   1800
caaacgaaag cagcaaattc aatagcaaat ttggcactga ttaaaacggt tttgtcacgt   1860
atttctaaca aacattcatt cgcaacaaaa ataataagag ttgatggaga tgataactat   1920
gcggtgctac aatttaatac agaggtgact aagcagatga tccaagacgt atcgaacgat   1980
gtaagagaaa cttatgcacg catgaatgct aaagttaaag ctctggtatc cacagtagga   2040
atagaaattg ctaaaaggta cattgcaggt ggaaaaatat tttttcgagc tggaataaat   2100
ctacttaata atgaaaagag agggcagagt acgcagtggg atcaagcagc aattttatat   2160
tcaaattata ttgtaaatag acttagagga tttgaaactg atagggagtt tattttaact   2220
aagataatgc agatgacgtc agtcgcaatt actggatcat taagactatt tccttctgaa   2280
cgcgtattaa ctacgaattc aacatttaaa gtatttgact cggaggattt tattatagag   2340
tacggaacga ctgatgacga agtatatata caaagagcgt tcatgtcttt atcaagtcag   2400
aaatcaggaa tagccgatga gatagcggca tcatcaacat ttaaaaatta cgtcacgaga   2460
```

-continued

```
ctatctgaac agttattatt ttcaaagaat aatatagtgt ccagaggaat agctttgact   2520

gaaaaagcga aattgaattc atacgctcca atatcgcttg agaaaagacg tgcacagata   2580

tcagctttat tgactatgtt gcagaaaccg gtcaccttca aatcaagtaa aataacaata   2640

aatgacatac tcagagatat aaaaccattt tttacagtaa gtgatgcaca cttacctata   2700

caataccaaa aatttatgcc aactttgcca gataacgtac agtatataat tcaatgtata   2760

ggatccagaa cttatcaaat tgaagatgac ggttcgaagt cagccatatc tagactaata   2820

tcaaagtatt cagtttataa gccatcaatt gaagaattgt ataaagtgat ttcattgcat   2880

gaaaacgaaa tacaattata tctgatttca ttaggaatac cgaaaataga cgctgacacg   2940

tatgttggat caaagattta ttctcaagat aagtatagaa tactagaatc atacgtgtac   3000

aatttattgt ccattaatta tggatgctat caattatttg atttcaattc accggacttg   3060

gagaagctga taagaatacc atttaaggga aaaataccag ctgttacatt catattacac   3120

ttatatgcaa agctagaagt tataaactac gctataaaaa atggttcatg gataagccta   3180

ttttgcaatt accctaaatc agaaatgata aaattatgga agaagatgtg gaacatcacg   3240

tcattacgtt cgccgtacac taacgcgaac ttctttcaag attagaacgc ttagatgtga   3300

cc                                                                  3302
```

```
<210> SEQ ID NO 2
<211> LENGTH: 2693
<212> TYPE: DNA
<213> ORGANISM: Rotavirus strain SA11

<400> SEQUENCE: 2

ggctattaaa ggctcaatgg cgtatcgaaa acgtggagcg cgtcgtgaga cgaatctaaa     60

acaagatgaa cgaatgcaag aaaaagaaga tagcaagaac attaataatg acagtcctaa    120

atcacaatta tcagaaaaag tattatctaa gaaagaagag ataattacag ataatcaaga    180

agaagttaag atatctgatg aggtaaaaaa atctaataaa gaagaatcga aacagttgtt    240

agaagtactt aaaacaaaag aggaacatca aaaagaagtt cagtatgaaa tattacaaaa    300

aactatccct acatttgaac caaaagagtc aatactcaaa aaattagaag acataaaacc    360

agaacaagca aagaaacaaa ctaaactgtt tcgaatattt gaaccgaaac aattgcctat    420

ttatagagct aatggagaaa gagagcttcg taatagatgg tattggaaat tgaaacgaga    480

tactcttcct gatggagatt atgatgttag agagtatttt ttaaatttat atgatcaagt    540

attaatggaa atgccggatt atctattact taaagatatg gctgtagaga ataaaaattc    600

aagggatgct ggcaaagtag ttgattctga aacagccgca atatgcgatg ctatttttca    660

agatgaagaa accgaaggtg cagtaagaag attcatagct gagatgagac aacgagttca    720

agctgatcga aatgtagtca attatccatc tatattgcat ccaattgacc atgcgtttaa    780

cgaatacttc ttacaacatc agttggtaga accattaaat aatgatatca ttttcaatta    840

cataccagag agaataagaa atgatgtcaa ctatatatta aatatggaca ggaatttacc    900

gtctactgct agatatatca gaccaaactt gctacaagat aggttaaatt tacatgataa    960

ttttgagtca ctctgggata ctataactac atctaattat attttagcaa gatctgtggt   1020

gccagaccta aaagaattag tatctactga ggcacaaatc cagaaaatgt cacaagattt   1080

gcaattggaa gctttgacaa tacaatcaga gactcagttt ttaacaggta taaactcaca   1140

agccgctaat gattgtttta aaactttgat tgctgctatg ttgagtcaga gaaccatgtc   1200

attagatttc gtaacgacaa attacatgtc acttatttca ggcatgtggt tactcactgt   1260
```

gattccaaat gatatgttta taagagaatc attagtagca tgtcaactag ccataataaa 1320
taccattgtt tatccggcat tcggaatgca aagaatgcat tataggaatg gtgatccaca 1380
gactcccttt caaattgcag agcaacagat tcaaaatttt caggtagcta attggttaca 1440
ttttgttaat tataatcagt ttagacaagt agtgattgat ggagtgttaa atcaagtctt 1500
gaatgataat ataagaaatg gtcatgtagt caaccaatta atggaagctc tgatgcaatt 1560
atctagacaa cagtttccca caatgccagt tgattataaa agatctatac agagaggaat 1620
tttgctgctt tctaacagac ttggtcagct tgtcgattta acaagattgt tatcatacaa 1680
ttatgagaca ttaatggcat gcataacaat gaatatgcag catgttcaaa cattaacaac 1740
tgaaaaattg caattaacat cagtaacatc attatgtatg ctaattggaa atgctacggt 1800
tataccgagt ccgcaaacat tgttccatta ctataatgtg aatgtcaatt ttcattcaaa 1860
ttataatgaa agaattaatg acgcagttgc aattataact gcggcaaata gattaaattt 1920
atatcaaaag aaaatgaaat caatagttga ggactttctg aaaagattac agatatttga 1980
tgttgcgaga gtaccagatg accaaatgta tagattgaga gatagattaa gactattacc 2040
agttgaaata agaagattag atatttttaa tttgatagca atgaatatgg aacagattga 2100
acgtgcatca gataaaattg cacaaggagt tataatagca taccgagata tgcagttaga 2160
acgagatgag atgtatggtt acgtcaatat tgccagaaac ttggacggat ttcaacaaat 2220
aaatcttgaa gaattgatga gatcaggaga ttatgctcaa attactaaca tgctacttaa 2280
taatcaacca gtagctttag ttggagcgct accatttata acggattcat cagtgatttc 2340
gttaatagct aaactagatg caaccgtttt tgcacagatt gtcaaactta gaaaggtcga 2400
cacgttaaaa cccatcctat ataagataaa ttcagattct aatgactttt atttggtggc 2460
taattatgat tggattccta catctactac aaaagtgtat aaacaagttc cacaacaatt 2520
tgattttaga gcgtcaatgc atatgttaac gtctaaccta acatttaccg tatattcaga 2580
tttgcttgcg ttcgtttcag ctgatactgt tgaaccaatt aatgctgttg cttttgataa 2640
tatgcgcatc atgaacgaat tgtaaacgcc aaccccattg tggagatatg acc 2693

<210> SEQ ID NO 3
<211> LENGTH: 2591
<212> TYPE: DNA
<213> ORGANISM: Rotavirus strain SA11

<400> SEQUENCE: 3
ggctattaaa gcagtaccag tagtgtgttt tacctctgat ggtgtaaaca tgaaagtact 60
agctttaaga cacagtgtgg ctcaagtgta tgcagacact caagtctacg ttcatgatga 120
tacaaaagat agttatgaaa acgctttttt aatctctaat cttacgaccc ataatatttt 180
atacttaaat tatagcatta aaacattaga aatattaaat aagtcaggaa tagctgcaat 240
tgctttacaa tcacttgaag aattattcac attaataagg tgtaatttca cttatgatta 300
tgaacttgat ataatatatt tacatgatta ttcatattat accaataatg aaattagaac 360
agaccaacat tggataacaa aaacaaatat tgaagaatat ttactacctg gatggaaatt 420
aacatatgtt ggttataatg gaagtgaaac tagaggacat tataactttt catttaaatg 480
tcaaaacgct gcaacagatg atgatctaat aattgaatac atttattcag aagcgttgga 540
cttccaaaat tttatgttaa aaaagataaa ggaaagaatg actacatcgt tgcctatagc 600
tagattatct aacagagtat ttagggataa gttattccca tcattattga aagaacataa 660

-continued

```
gaatgtagtg aacgttggtc cgcgtaatga atctatgttt acatttttaa attatccaac    720
tataaaacaa ttttcaaatg gtgcgtattt agtaaaagat actataaaat taaaacaaga    780
acgatggtta ggtaaaagga tatctcagtt tgatattggt cagtataaaa atatgctgaa    840
tgttcttaca gcaatttatt attactataa tttatataaa agtaaaccaa ttatatatat    900
gatcggatct gctccatctt attggatata tgacgttagg cattattccg atttttttctt   960
tgaaacttgg gatccattgg acacaccata ttcatcaatc catcacaaag aattattttt   1020
tataaatgat gtgaagaaac tgaaggataa ctcaatattg tatattgata taagaaccga   1080
taggggcaat gctgattgga aaaaatggag aaagacagta gaagaacaaa ctattaataa   1140
tttggacata gcttatgaat atttacgaac gggtaaagcg aaggtgtgtt gtgttaagat   1200
gacagctatg gatttggaac tgccaatttc agctaaatta ctgcaccacc caactacgga   1260
aataagatca gaattttatt tattactaga tacttgggat ttaactaaca ttaggaggtt   1320
cattcctaaa ggcgtgttat attcatttat aaacaatata ataactgaaa atgtgtttat   1380
tcaacaacca tttaaagtaa aagtactgaa tgatagttat attgtagcgt tatatgcatt   1440
atcaaatgat tttaataata gatcagaagt aattaaatta attaataatc agaaacaatc   1500
tctaataact gttagaataa ataatacgtt taaggatgaa ccaaaagttg ggttcaaaaa   1560
tatctatgat tggacctttc ttccaaccga ctttgatacc aaagaagcta taattacttc   1620
atacgacggt tgtttaggac tctttggttt gtctatatcg ttagcatcaa aaccaacagg   1680
gaataatcat ttattcattt taagtggtac agataagtat tataaattgg atcaatttgc   1740
taatcacacc agtatatcga gaagatcaca ccaaattagg ttttcggaat ctgctacttc   1800
atattcaggt tatatattta gagatttgtc caataataat tttaatctaa ttggtactaa   1860
tatagagaat tcagtatcag gtcatgtata taatgcttta atttattata gatataatta   1920
ttcatttgat cttaaacgct ggatttattt acattctata gataaagttg atatagaagg   1980
aggaaagtat tatgaacacg caccaataga attaatttat gcatgtagat cagcaaaaga   2040
atttgctaca ttgcaggatg acttaactgt attgagatat tcaaacgaaa tagagaatta   2100
tattaataca gtatatagta taacatacgc tgatgatccg aattacttta tcggaataca   2160
atttagaaat ataccatata aatatgatgt taaaataccg catttaacct tcggagtatt   2220
acatatttct gataacatgg tgccagacgt gattgacata ctaaagataa tgaagaatga   2280
attatttaaa atggatatta cgaccagtta tacatatatg ttatcagatg gaatctacgt   2340
agcaaatgtt agtggagtat tatctacata ctttaaaatc tataacgtat tttataaaaa   2400
tcaaataact tttggccaat ccagaatgtt tattccgcac ataacattaa gcttcaataa   2460
catgagaaca gtaaggatag agactactaa attacaaatt aaatccattt atttaagaaa   2520
gattaagggt gatacagtgt ttgatatggt tgagtgagct aaaaacttaa cacactagtc   2580
atgatgtgac c                                                         2591
```

```
<210> SEQ ID NO 4
<211> LENGTH: 2362
<212> TYPE: DNA
<213> ORGANISM: Rotavirus strain SA11

<400> SEQUENCE: 4

ggctataaaa tggcttcgct catttataga caattgctca cgaattctta tacagtagat     60
ttatccgatg agatacaaga gattggatca actaaatcac aaaatgtcac aattaatcct    120
ggaccatttg cgcaaacagg ttatgctcca gttaactggg gacctggaga aattaatgat    180
```

-continued

```
tctacgacag ttggaccatt gctggatggg ccttatcaac caacgacatt caatccacca    240

gtcgattatt ggatgttact ggctccaacg acacctggcg taattgttga aggtacaaat    300

aatacagata gatggttagc cacaatttta atcgagccaa atgttcagtc tgaaaataga    360

acttacacta tatttggtat tcaagaacaa ttaacggtat ccaatacttc acaagaccag    420

tggaaattta ttgatgtcgt aaaaacaact gcaaatggaa gtataggaca atatggacca    480

ttactatcca gtccgaaatt atatgcagtt atgaagcata atgaaaaatt atatacatat    540

gaaggacaga cacctaacgc taggacagca cattattcaa caacgaatta tgattctgtt    600

aacatgactg ctttttgtga cttttatata attcctagat ctgaagagtc taaatgtacg    660

gaatacatta ataatggatt accaccaata caaaatacta gaaatgttgt accattatcg    720

ttgactgcta gagatgtaat acactataga gctcaagcta atgaagatat tgtgatatcc    780

aagacatcat tatggaaaga aatgcaatat aatagagata taactattag atttaaattt    840

gcaaatacaa ttataaaatc aggagggctg ggatataagt ggtcagaaat atcatttaag    900

ccagcgaatt atcaatacac atatactcgt gatggtgaag aagttaccgc acatactact    960

tgttcagtga atggcgttaa tgacttcagt tttaatggag gatatttacc aactgatttt   1020

gttgtatcta aatttgaagt aattaaagag aattcatacg tctatatcga ttactgggat   1080

gattcacaag catttcgtaa cgtggtgtat gtccgatcgt tagcagcaaa cttgaattca   1140

gttatgtgta ctggaggcag ctataatttt agtctaccag ttggacaatg gcctgtttta   1200

actgggggag cagtttcttt acattcagct ggtgtaacac tatctactca atttacagat   1260

ttcgtatcat taaattcatt aagatttaga tttagactag ctgtcgaaga accacacttt   1320

aaactgacta gaactagatt agatagattg tatggtctgc ctgctgcaga tccaaataat   1380

ggtaaagaat attatgaaat tgctggacga ttttcactta tatcattagt gccatcaaat   1440

gatgactatc agactcctat agcaaactca gttactgtac gacaagattt agaaaggcag   1500

ttaggagaac taagagaaga gtttaacgct ttgtctcaag aaattgcaat gtcgcagtta   1560

atcgatttag cgcttctacc attagatatg ttctcaatgt tttctggcat taaaagtact   1620

attgatgctg caaaatcaat ggctactaat gttatgaaaa aattcaaaaa gtcaggatta   1680

gcgaattcag tttcaacact gacagattct ttatcagacg cagcatcatc aatatcaaga   1740

ggttcatcta tacgttcgat tggatcttca gcatcagcat ggacggatgt atcaacacaa   1800

ataactgata tatcgtcatc agtaagttca gtttcgacac aaacgtcaac tatcagtaga   1860

agattgagac taaaggaaat ggcaacacaa actgagggta tgaattttga tgatatatca   1920

gcggctgttt tgaagactaa gatagataaa tcgactcaaa tatcaccaaa cacaatacct   1980

gacattgtta ctgaagcatc ggaaaaattc ataccaaata gggcttaccg cgttataaac   2040

aacgatgatg tgtttgaagc tggaattgat gggaaatttt ttgcttataa agtggataca   2100

tttgaggaaa taccatttga tgtacaaaaa ttcgctgact tagttacaga ttctccagta   2160

atatccgcta taattgattt taaaacactt aaaaatttga acgataatta cggcattact   2220

aagcaacaag catttaatct tttaagatct gacccaagag ttttacgtga attcattaat   2280

caggacaatc ctataattag aaatagaatt gaacaactga ttatgcaatg caggttgtga   2340

gtaatttcta gaggatgtga cc                                             2362
```

<210> SEQ ID NO 5
<211> LENGTH: 1610
<212> TYPE: DNA

<213> ORGANISM: Rotavirus strain SA11

<400> SEQUENCE: 5

```
ggcttttttt tgaaaagtct tgtgttagcc atggctactt ttaaagatgc atgctttcat      60
tatcgtagat taactgcttt aaatcggaga ttatgcaaca ttggtgcaaa ttctatttgg     120
atgccagttc ctgatgcgaa aattaagggg tggtgtttag aatgttgtca aatagctgat     180
ttaacccatt gttatggttg ctcattgccg catgtttgca aatggtgtgt tcagaacaga     240
agatgcttcc ttgacaatga acctcatttg cttaagctta gaactgtgaa acatccaatt     300
accaaagaca aattacagtg tatcatagac ttgtacaata taatatttcc aattaatgat     360
aaagtaatta gaaaatttga aagaatgata aagcaaagag aatgtaggaa tcaatataaa     420
attgaatggt ataatcattt gctgctccca attacattaa atgctgctgc atttaagttt     480
gatgaaaata atctttatta tgtttttggg ttatatgaga aatcagtcag tgatatatat     540
gctccatata gaattgttaa ctttataaat gaatttgata aattattgct tgatcatatt     600
aactttacaa gaatgtccaa tctaccaata gagttgagaa accattacgc aaagaaatac     660
ttccaattat caagactgcc atcatcaaaa ctaaagcaaa tttacttttc agattttact     720
aaagaaactg tgatttttaa tacttataca aaaacgccag gaagatcaat atacagaaat     780
gtaactgaat ttaattggag agatgaattg gagctttatt ctgatttaaa aaatgataag     840
aataaattaa ttgctgcaat gatgacgagt aagtatactc ggttctatgc tcatgataat     900
aattttggaa ggttgaaaat gacaatattt gagttgggac atcattgtca gcctaactac     960
gtggcatcta atcacccagg caatgcttcc gatatccagt actgtaaatg gtgtaatata    1020
aaatattttc ttagtaaaat tgattggcgg attcgtgata tgtataattt attgatggaa    1080
tttattaagg attgttataa aagtaatgtt aacgttggac attgtagttc tgttgaaaac    1140
atatatcctt taattaaaag attaatttgg agtttgttta ctaatcacat ggatcaaaca    1200
attgaagaag tgtttaatca catgtcgcca gtgtcagttg aaggtacgaa tgtcatcatg    1260
ttgattcttg gattgaatat tagtttgtat aatgaaatta agcgcacttt gaatgtagat    1320
agcataccaa tggtacttaa tttaaatgaa ttcagtagta tagttaaatc aattagcagt    1380
aaatggtata atgttgatga attggataaa ttgccaatgt caataaaatc aacggaggaa    1440
ctgattgaaa tgaagaattc tggaacttta actgaagaat ttgagctact gatctccaac    1500
tcagaagatg acaatgagtg aaattatgtc actatctaat tatacagtat ttagccatca    1560
caagaccgtc cagactagag tagcgcctag ctggcaaaat actgtgaacc                1610
```

<210> SEQ ID NO 6
<211> LENGTH: 1356
<212> TYPE: DNA
<213> ORGANISM: Rotavirus strain SA11

<400> SEQUENCE: 6

```
ggcttttaaa cgaagtcttc aacatggatg tcctatactc tttgtcaaag actcttaaag      60
acgctagaga caaaattgtc gaaggcacat tgtattctaa cgtgagtgat ctaattcaac     120
aatttaatca aatgataatt actatgaatg gaaatgaatt tcaaactgga ggaatcggta     180
atttgccaat tagaaactgg aattttaatt tcgggttact tggaacaact ttgctgaact     240
tagacgctaa ttatgttgaa acggcaagaa atacaattga ttatttcgtg gattttgtag     300
acaatgtatg catggatgag atggttagag aatcacaaag gaacggaatt gcacctcaat     360
cagactcgct aagaaagctg tcagccatta aattcaaaag aataaatttt gataattcgt     420
```

-continued

```
cggaatacat agaaaactgg aatttgcaaa atagaagaca gaggacaggt ttcacttttc    480
ataaaccaaa catttttcct tattcagcat catttacact aaatagatca caacccgctc    540
atgataattt gatgggcaca atgtggttaa acgcaggatc ggaaattcaa gtcgctggat    600
ttgactactc atgtgctatt aacgcaccag ccaatataca acaatttgag catattgtgc    660
cactccgaag agtgttaact acagctacga taactcttct accagacgcg gaaaggttta    720
gttttccaag agtgatcaat tcagctgacg ggcaactac atggtttttc aacccagtga    780
ttctcaggcc gaataacgtt gaagtggagt ttctattgaa tggacagata ataaacactt    840
atcaagcaag atttggaact atcgtagcta gaaattttga tactattaga ctatcattcc    900
agttaatgag accaccaaac atgacaccag cagtagcagt actattcccg aatgcacagc    960
cattcgaaca tcatgcaaca gtgggattga cacttagaat tgagtctgca gtttgtgagt   1020
ctgtactcgc cgatgcaagt gaaactctat tagcaaatgt aacatccgtt aggcaagagt   1080
acgcaatacc agttggacca gtctttccac caggtatgaa ctggactgat ttaatcacca   1140
attattcacc gtctagggag gacaatttgc aacgcgtatt tacagtggct tccattagaa   1200
gcatgctcat taaatgagga ccaagctaac aacttggtat ccaactttgg tgagtatgta   1260
gctatatcaa gctgtttgaa ctctgtaagt aaggatgcgt atacgcattc gctacacaga   1320
gtaatcactc agatggtata gtgagaggat gtgacc                             1356
```

<210> SEQ ID NO 7
<211> LENGTH: 1105
<212> TYPE: DNA
<213> ORGANISM: Rotavirus strain SA11

<400> SEQUENCE: 7

```
ggcatttaat gcttttcagt ggttgatgct caagatggag tctacgcaac agatggccgt     60
ctcaattatt aactcttctt ttgaagctgc agttgtagct gcaacctcag ctcttgagaa    120
tatgggaata gaatatgatt atcaggatat atattctaga gtaaagaata aatttgattt    180
tgtgatggac gattctggtg ttaaaaataa tctgattggt aaagcaataa ctattgatca    240
agctttgaat aataaatttg gatctgctat aagaaataga aactggcttg ctgatacttc    300
tagagcagct aaattagatg aggatgtaaa caaactaaga atgatgttat catcaaaagg    360
aattgatcaa aaaatgagag ttttaaacgc atgcttcagt gtaaaaagaa tacctggaaa    420
atcatcatct attattaaat gcacaaaatt gatgcgtgat aaattggaac gtggtgaagt    480
tgaagtggat gattcatttg tggatgaaaa aatggaagtg gataccattg actggaaatc    540
gcgctatgag caattggagc aaaggtttga atcattgaaa tccagggtaa atgaaaaata    600
taataattgg gtgttgaaag caagaaaaat gaatgaaaat atgcattctc ttcaaaatgt    660
catctctcaa cagcaagcac atatagctga gcttcaagtg tacaataata aactagaacg    720
tgatttgcaa aataaaattg gatcccttac ttcttcgatt gaatggtatt taagatcaat    780
ggaattagac cctgaaataa aggcagacat tgaacagcaa attaactcaa ttgatgcgat    840
aaatccattg cacgcttttg atgacttaga atcagtaata cgtaatttga tatctgatta    900
tgacaaatta ttccttatgt tcaaaggatt aatacagaga tgtaattatc aatattcatt    960
tggttgcgaa taaccatttt gatacatgtt gaacaatcaa atacagtgtt agtatgttgt   1020
catctatgca taaccctcta tgagcacaat agttaaaagc taacactgtc aaaaacctaa   1080
atggctatag ggcgttatg tggcc                                          1105
```

<210> SEQ ID NO 8
<211> LENGTH: 1059
<212> TYPE: DNA
<213> ORGANISM: Rotavirus strain SA11

<400> SEQUENCE: 8

```
ggcttttaaa gcgtctcagt cgccgtttga gccttgcggt gtagccatgg ctgagctagc     60
ttgcttttgc tatcctcatt tggagaatga tagctataaa tttattcctt ttaataattt    120
agctattaaa gctatgctga cagctaaagt agacaaaaag gacatggata agttttatga    180
ttcaattatt tatggaatag caccgcctcc tcaatttaag aaacggtata atactaatga    240
taattcaaga ggcatgaatt ttgaaacaat tatgtttact aaggtggcta tgttgatatg    300
tgaagctcta aattcattga aagtgacgca agcaaacgtc tctaatgtat tatcacgagt    360
agtatcaata aggcatttag aaaatttggt gatacgtaaa gaaaatccac aggatattct    420
atttcattca aaagatttac ttttgaaatc aacactgatt gctattggac agtctaaaga    480
aattgaaact acaataactg cagaaggagg agaaattgta tttcaaaacg ctgccttcac    540
catgtggaaa ctaacttatt tagaacatca attgatgcca attctggatc agaattttat    600
tgaatataaa gttacattga acgaagataa accaatttca gatgttcatg ttaaagaatt    660
agtcgctgaa cttcgatggc aatataacaa gtttgctgta atcacacatg gtaagggtca    720
ttatagaatt gtaaagtatt catcagttgc taatcacgct gacagagtat atgcaacttt    780
caagagtaat gttaaaactg gagttaataa tgattttaac ctacttgatc aaagaattat    840
ttggcaaaac tggtatgcat ttacatcatc aatgaaacag ggtaatacac ttgacgtgtg    900
taaaaggttg cttttccaaa aaatgaaacc agaaaaaaat ccatttaaag ggctgtcaac    960
ggatagaaaa atggacgaag tttctcaagt tggcgtttaa ttcgctatca atttgaggat   1020
gatgatggct tagcaagaat agaaagcgct tatgtgacc                          1059
```

<210> SEQ ID NO 9
<211> LENGTH: 1063
<212> TYPE: DNA
<213> ORGANISM: Rotavirus strain SA11

<400> SEQUENCE: 9

```
ggctttaaaa agagagaatt tccgtttggc tagcggttag ctccttttaa tgtatggtat     60
tgaatatacc acagttctaa cctttctgat atcgattatt ctactaaatt acatacttaa    120
atcattaact agaataatgg actttataat ttatagattt ctttttataa ttgtgatatt    180
gtcaccattt ctcagagcac aaaattatgg tattaatctt ccaatcacag gctccatgga    240
cattgcatac gctaattcaa cgcaagaaga accattcctc acttctacac tttgcctata    300
ttatccgact gaggctgcga ctgaaataaa cgataattca tggaaagaca cactgtcaca    360
actatttctt acgaaagggt ggccaactgg atccgtatat tttaaagaat atactaacat    420
tgcatcgttt tctgttgatc cgcagttgta ttgtgattat aacgtagtac taatgaaata    480
tgacgcgacg ttgcaattgg atatgtcaga acttgcggat ctaatattaa acgaatggtt    540
gtgtaatcca atggatatta ctctgtatta ttatcagcaa actgacgaag cgaataaatg    600
gatatcaatg ggctcatcat gtacaattaa agtatgtcca cttaatacac aaactcttgg    660
aattggatgc ttgacaactg atgctacaac ttttgaagaa gttgcgacag ctgaaaagtt    720
ggtaattact gacgtggttg atggcgttaa tcataagctg gatgtcacaa cagcaacgtg    780
tactattaga aactgtaaga aattgggacc aagagaaaac gtagccgtta tacaagttgg    840
```

-continued

```
tggttctgac atcctcgata taactgctga tccaactact gcaccacaga cagaacggat    900

gatgcgaatt aactggaaaa aatggtggca agttttttat actgtagtag actatgtaga    960

tcagataata caagttatgt ccaaaagatc aagatcacta aattcagcag cattttatta   1020

cagagtgtag gtataactta ggttagaatt gtatgatgtg acc                     1063
```

<210> SEQ ID NO 10
<211> LENGTH: 751
<212> TYPE: DNA
<213> ORGANISM: Rotavirus strain SA11

<400> SEQUENCE: 10

```
ggcttttaaa agttctgttc cgagagagcg cgtgcggaaa gatggaaaag cttaccgacc     60

tcaattatac attgagtgta atcactctaa tgaacaatac attgcacaca atacttgagg    120

atccaggaat ggcgtatttt ccttatatag catctgtctt aacagttttg tttgcgctac    180

ataaagcatc cattccaaca atgaaaattg cattgaaaac gtcaaaatgt tcatataaag    240

tggtgaaata ttgtattgta acaattttta atacgttgtt aaaattggca ggttataaag    300

agcagataac tactaaagat gagatagaaa agcaaatgga cagagtagtc aaagaaatga    360

gacgccagct agaaatgatt gacaaattga ctacacgtga aattgaacaa gtagagttgc    420

ttaaacgcat ttacgataaa ttgacggtgc aaacgacagg tgaaatagat atgacaaaag    480

agatcaatca aaaaaacgtg agaacgctag aagaatggga aagtggaaaa aatccttatg    540

aaccaagaga agtgactgca gcaatgtaag aggttgagct gccgtcgact gtcctcggaa    600

gcggcggagt tctttacagt aagcaccatc ggacctgatg gctgactgag aagccacagt    660

cagccatatc gcgtgtggct caagccttaa tcccgtttaa ccaatccggt cagcaccgga    720

cgttaatgga aggaacggtc ttaatgtgac c                                   751
```

<210> SEQ ID NO 11
<211> LENGTH: 667
<212> TYPE: DNA
<213> ORGANISM: Rotavirus strain SA11

<400> SEQUENCE: 11

```
ggcttttaaa gcgctacagt gatgtctctc agtattgacg tgacgagtct tccttctatt     60

ccttcaacta tatataagaa tgaatcgtct tcaacaacgt caactctttc tggaaaatct    120

attggtagga gtgaacagta catttcacca gatgcagaag cattcaataa atacatgctg    180

tcgaagtctc cagaggatat tggaccatct gattctgctt caaacgatcc actcaccagt    240

ttttcgatta gatcgaatgc agttaagaca aacgcagacg ctggcgtgtc tatggattca    300

tcagcacaat cacgaccttc aagtaatgtc ggatgcgatc aagtggattt ctccttaaat    360

aaaggcttaa aagtaaaagc taatttggac tcatcaatat caatatctac ggatactaaa    420

aaggagaaat caaaaacaaa ccataaaagt aggaagcact acccaagaat tgaagcagag    480

tctgattcag atgattatgt actggatgat tcagatagtg atgatggtaa atgtaagaac    540

tgtaaatata agaagaaata cttcgcatta agaatgagaa tgaaacaagt cgcaatgcaa    600

ttgattgaag atttgtaagt ctgacctggg aacacactag ggagctcccc actcccgttt    660

tgtgacc                                                              667
```

<210> SEQ ID NO 12
<211> LENGTH: 516
<212> TYPE: DNA

<213> ORGANISM: Oplophorus gracilirostris

<400> SEQUENCE: 12
atggtcttca cactcgaaga tttcgttggg gactggcgac agacagccgg ctacaacctg 60
gaccaagtcc ttgaacaggg aggtgtgtcc agtttgtttc agaatctcgg ggtgtccgta 120
actccgatcc aaaggattgt cctgagcggt gaaaatgggc tgaagatcga catccatgtc 180
atcatcccgt atgaaggtct gagcggcgac caaatgggcc agatcgaaaa aatttttaag 240
gtggtgtacc ctgtggatga tcatcacttt aaggtgatcc tgcactatgg cacactggta 300
atcgacgggg ttacgccgaa catgatcgac tatttcggac ggccgtatga aggcatcgcc 360
gtgttcgacg gcaaaaagat cactgtaaca gggaccctgt ggaacggcaa caaaattatc 420
gacgagcgcc tgatcaaccc cgacggctcc ctgctgttcc gagtaaccat caacggagtg 480
accggctggc ggctgtgcga acgcattctg gcgtga 516

<210> SEQ ID NO 13
<211> LENGTH: 516
<212> TYPE: DNA
<213> ORGANISM: Artificial sequence
<220> FEATURE:
<223> OTHER INFORMATION: Rv-NLuc

<400> SEQUENCE: 13
atggtcttta cgctcgaaga ttttgttggg gattggagac agacagctgg atacaactta 60
gatcaagttc ttgaacaggg aggtgtttca agtttgtttc agaatctcgg ggtgtcagta 120
actccgatcc aaaggattgt tttaagaggt gaaaatgggc ttaaaattga catccatgtc 180
attataccat atgaaggttt gagcggagat caaatgggac aaatagaaaa aatttttaag 240
gttgtttacc ctgtggatga tcatcatttt aaagtgatac tgcactatgg aacattggta 300
attgatgggg ttacgccaaa tatgatcgat tattttggaa gaccatatga aggcattgca 360
gtgttcgacg gaaaaaagat cactgtaact gggactttgt ggaatggcaa taaaattatc 420
gacgagcgcc tgataaaccc agatggctct ttactgttca gagtaacaat taacggagtg 480
accggctggc ggttatgtga aagaattctt gcttga 516

<210> SEQ ID NO 14
<211> LENGTH: 696
<212> TYPE: DNA
<213> ORGANISM: Zoanthus sp.

<400> SEQUENCE: 14
atggctcaga gcaagcacgg cctgaccaag gagatgacca tgaagtacag aatggagggc 60
tgcgtggacg gccacaagtt cgtgatcacc ggcgagggca tcggctaccc cttcaagggc 120
aagcaggcca tcaacctgtg cgtggtggag ggcggccccc tgcccttcgc cgaggacatc 180
ctgagcgccg ccttcatgta cggcaacaga gtgttcaccg agtaccccca ggacatcgtg 240
gactacttca agaacagctg ccccgccggc tacacctggg acagaagctt cctgttcgag 300
gacggcgccg tgtgcatctg caacgccgac atcaccgtga gcgtggagga gaactgcatg 360
taccacgaga gcaagttcta cggcgtgaac ttccccgccg acggccccgt gatgaagaag 420
atgaccgaca actgggagcc cagctgcgag aagatcatcc ccgtgcccaa gcagggcatc 480
ctgaagggcg acgtgagcat gtacctgctg ctgaaggacg gcggcagact gagatgccag 540
ttcgacaccg tgtacaaggc caagagcgtg cccagaaaga tgcccgactg gcacttcatc 600
cagcacaagc tgaccagaga ggacagaagc gacgccaaga accagaagtg gcacctgacc 660
gagcacgcca tcgccagcgg cagcgccctg ccctga 696

<210> SEQ ID NO 15
<211> LENGTH: 696
<212> TYPE: DNA
<213> ORGANISM: Artificial sequence
<220> FEATURE:
<223> OTHER INFORMATION: Rv-ZsGreen

<400> SEQUENCE: 15
atggctcagt caaaacatgg acttactaaa gaaatgacta tgaagtatag aatggagggg 60
tgtgttgatg gtcataaatt tgtgattacg gggggaaggaa taggataccc atttaagggt 120
aaacaagcta taaacttatg tgtggttgaa ggaggtccat tgccttttgc tgaagatata 180
ttgtcagcag cttttatgta tgggaataga gtgttcactg aatacccaca agatattgtt 240
gattatttca aaaatagttg tcctgcaggg tatacatggg atagatcgtt tttatttgaa 300
gatggtgctg tttgtatttg taatgcagat ataactgtat ccgtggaaga gaactgtatg 360
taccatgagt caaaatttta cggagttaat tttcctgctg atggaccagt tatgaaaaag 420
atgactgata attgggaacc ttcatgtgaa aaaattatcc cagttcctaa acaaggaata 480
ttgaaagggg atgtatcaat gtatttactt ttaaaggatg gggtagatt gcggtgccaa 540 ttcgacactg tttataaagc aaagtctgtt ccaaggaaaa tgccagattg gcactttatc 600
cagcataagc tgactcggga ggatcgcagt gacgctaaaa atcagaagtg gcatttaaca 660
gagcatgcta ttgctagtgg atcagctttg ccatga 696

<210> SEQ ID NO 16
<211> LENGTH: 699
<212> TYPE: DNA
<213> ORGANISM: Anemonia sulcata

<400> SEQUENCE: 16
atggcctctt tgctgaagaa gaccatgccc ttcaggacca ccatcgaggg caccgtgaac 60
ggccactact tcaagtgcac cggcaagggc gagggcaacc ccctggaggg cacccaggag 120
atgaagatcg aggtgatcga gggcggcccc ctgcccttcg ccttccacat cctgtccacc 180
tcctgcatgt acggctccaa ggccttcatc aagtacgtgt ccggcatccc cgactacttc 240
aagcagtccc tccccgaggg cttcacctgg gagcgcacca ccacctacga ggacggcggc 300
ttcctgaccg cccaccagga cacctccctg gacggcgact gcctggtgta caaggtgaag 360
atcctgggca acaacttccc cgccgacggc cccgtgatgc agaacaaggc cggccgctgg 420
gagccctcca ccgagatcgt gtacgaggtg gacggcgtgc tgcgcggcca gtccctgatg 480
gccctggagt gccccggcgg tcgccacctg acctgccacc tgcacaccac ctaccgctcc 540
aagaagcccg cctccgccct gaagatgccc ggcttccact tcgaggacca ccgcatcgag 600
atcctggagg aggtggagaa gggcaagtgc tacaagcagt acgaggccgc cgtgggccgc 660
tactgcgacg ccgccccctc caagctgggc cacaactga 699

<210> SEQ ID NO 17
<211> LENGTH: 699
<212> TYPE: DNA
<213> ORGANISM: Artificial sequence
<220> FEATURE:
<223> OTHER INFORMATION: Rv-AsRed

<400> SEQUENCE: 17

-continued

```
atggcttctt tgctaaagaa aacaatgcca tttagaacta cgatcgaagg aactgtaaat      60

ggacattact ttaaatgtac gggcaaaggc gaaggcaatc cattagaagg cacgcaagaa     120

atgaagatag aagttattga aggaggacca ttaccttttg cattccatat tttatcaact     180

agttgcatgt atggatccaa agctttcata aaatatgtta gcggtattcc agattatttc     240

aaacagtcac tcccagaagg atttacatgg gaaaggacta ccacttatga ggacgggggt     300

tttcttacgg ctcatcaaga tacatcactt gatggagact gtttagttta caaagtaaaa     360

attttgggta acaactttcc ggcagatggg cctgtgatgc agaataaggc tgggcggtgg     420

gaacccagta cagaaatagt gtatgaagtt gatggagtgt tgagaggaca atcgctgatg     480

gcattagaat gtccaggagg tcgccatctt acttgtcact tgcatactac ttatagaagt     540

aagaaaccag cttcagcttt gaagatgcct ggatttcatt ttgaagatca cagaattgag     600

atattagaag aggttgaaaa aggaaaatgc tacaagcaat atgaagcagc ggttggtaga     660

tattgtgacg cagctccatc taaattggga cataattga                            699
```

```
<210> SEQ ID NO 18
<211> LENGTH: 1653
<212> TYPE: DNA
<213> ORGANISM: Artificial sequence
<220> FEATURE:
<223> OTHER INFORMATION: Rv-Akaluc

<400> SEQUENCE: 18

atggaagatg caaaaaatat taagaaagga ccagcgccgt tttatccact tgaagatggg      60

actgcaggcg aacaactgca taaagctatg aaaagatatg cattggttcc aggagcaata     120

gcttttactg acgcacatat tcaggttgat gttacttatg ctgaatattt tgagatgtca     180

gttcggttag cagaagctat gaggagatat gggttaaata caaatcatcg gatagttgtg     240

tgtagtgaaa atagttcgca gttctttatg ccagtgttgg gtgcattatt tataggtgtt     300

gctgtggcac cagctaatga tatatataac gaaagagaac tgctgaatag catgggcatt     360

tcacagccta ctgtcgtatt tgtgagcaag aaagggttaa gaaaagtcct taacgtgcaa     420

aagaaactac cgattataag aaaaattata attatggata gcaaaactga ttaccagggc     480

tttcaatcaa tgtacacctt tgttacttcc catttgccac caagttttaa tgaatacgat     540

tttgttcccg agtcattcga tcgggataaa actattgcac tgataatgaa tagtagtggt     600

agtacaggat taccaaaggg agtagctcta ccgcatagaa ctgcttgtgt tagatttagt     660

catgctagag atccaatatt tggctatcag aatatcccag acactgctat actcagtgtg     720

gtgccatttc atcacgggtt tggaatgttt accacgttag gatatttgat atgcggattt     780

cgggttgtgc ttatgtatag atttgaagaa gagctatttt tgagaagttt gcaagattat     840

aagattcaat ctgcattatt ggttccaaca ctattttcat gtcttgctaa atcaactctc     900

atagacaaat atgatctatc ttcattgaga gaaattgcaa gcggcggggc gccgctcagc     960

aaggaggtag gtgaagcagt cgctaaaaga tttagactac caggcattag acaaggctat    1020

ggcttaacag aaacaaccaa tgcagttatg ataactcctg agggggatcg taagcctgga    1080

tcagtaggca aagtcgtgcc attctttgaa gctaaggttg tagatttggt cactggtaag    1140

acactgggtg ttaaccaaag aggtgagttg tgtgtccgtg gacctatgat tatgagtgga    1200

tacgttaata atccagaggc tacgaatgct cttattgaca aagatggatg gttacattct    1260

ggagatatag catattggga tgaagacgaa cacttcttta tagttgatcg gttaaagagt    1320

ctgattaaat acaaaggata tcaggtagct ccagctgaat tggaaggaat tctgttacaa    1380
```

-continued cacccatata ttttcgatgc tggagtcgct ggattacctg atgacgatgc tggagagtta 1440
ccagcagcag ttgttgtgtt ggaacatggt aaaaccatga ctgaaaaaga gatagtggat 1500
tatgttgcat cacaagttac aacggctaag aaattgcgcg gtggtgttgt gtttgttgat 1560
gaagtcccta gaggatcgac tggaaaatta gatgctagaa agattagaga aattctcact 1620
aaagctaaga aagatggaaa aattgcagtt tga 1653

<210> SEQ ID NO 19
<211> LENGTH: 1623
<212> TYPE: DNA
<213> ORGANISM: Artificial sequence
<220> FEATURE:
<223> OTHER INFORMATION: Rv-NoV VP1

<400> SEQUENCE: 19
atgaaaatgg catcgagtga tgctaatcca tctgatgggt cagcagctaa tcttgttcca 60
gaggttaaca atgaagttat ggctctggag ccagttgttg gtgctgctat tgcggcacct 120
gtagcgggac aacaaaatgt aattgatccg tggattagaa ataattttgt acaagctcct 180
ggtggagaat ttacggtatc acctagaaat gctccaggag aaatattatg gagtgctcct 240
ttgggacctg atctaaatcc atacttatca catttggcaa gaatgtataa tggttatgca 300
ggtggatttg aagtgcaggt aattttggct gggaacgcgt ttactgctgg gaaggtcata 360
tttgcagcag ttccaccaaa ttttccaact gaaggattga gtccaagcca ggttaccatg 420
ttcccacata tagtagtaga cgttagacag ttagaacctg tgttgattcc attaccagat 480
gttcggaaca atttttatca ttataatcaa tcaaatgatc caaccattaa attgatagca 540
atgttgtata cgccacttag agctaataat gctggggatg atgtttttac agtttcttgc 600
cgggttttaa cgagaccatc acctgacttt gattttatat ttttagtgcc accgactgtt 660
gagtcaagaa ctaaaccatt ctctgtccca gttttaactg ttgaggaaat gactaattca 720
agattcccaa ttcctttgga aaagttgttc acgggtccaa gtagtgcatt tgttgttcaa 780
ccacaaaatg gaagatgtac gactgatggc gtgcttttag gcactaccca attatctcct 840
gttaatatct gtacttttag aggagatgtt actcatataa ctggtagtcg taactataca 900
atgaatttgg cttctcaaaa ctggagtaat tatgatccaa cagaagatat tccagcacct 960
ctaggaactc cagattttgt ggggaaaatt caaggagtgc tcactcaaac tacacggaca 1020
gatggatcaa cacgtggaca taaagcaact gtgtacactg ggtcagcaga ctttgctcca 1080
aaactgggta gagttcagtt tgaaactgat acagaccatg attttgaagc taatcaaaat 1140
acaaaattta ccccagttgg tgtcatacaa gatggaggaa ctacccaccg caatgaacca 1200
caacagtggg tactcccaag ttattcagga agaaacactc ctaatgtgca tttagctccg 1260
gctgtagctc caacttttcc aggagaacaa cttcttttct tcagatccac tatgccagga 1320
tgctcagggt atccaaacat ggatttggat tgtttacttc ctcaggaatg ggtgcagtac 1380
ttttaccaag aggcagcacc agcacagtct gatgtggctc tgttaagatt tgtgaatcca 1440
gatacaggta gagttttgtt tgaatgtaag cttcacaaat caggatatgt tacagtggct 1500
catactggcc aacatgattt ggtcatccct ccgaatggat attttaggtt tgattcctgg 1560
gttaatcagt tttatacgct tgctccaatg ggaaatggaa cggggagaag acgtgcacta 1620
tga 1623